United States Patent [19]

Brossia et al.

[11] Patent Number: 5,005,005
[45] Date of Patent: Apr. 2, 1991

[54] FIBER OPTIC PROBE SYSTEM

[76] Inventors: Charles E. Brossia, 1748 E. Ross La., Highlands Ranch, Colo. 80126; Samuel C. Wu, 10205 W. Exposition Ave., Lakewood, Colo. 80226

[21] Appl. No.: 317,426

[22] Filed: Mar. 1, 1989

Related U.S. Application Data

[63] Continuation-in-part of Ser. No. 838,283, Mar. 10, 1986, Pat. No. 4,851,817.

[51] Int. Cl.$^5$ .................... G08B 21/00; G08B 19/02
[52] U.S. Cl. .................... 340/604; 250/573; 340/605; 340/619; 340/583
[58] Field of Search ............... 340/583, 619, 604–605, 340/600–601, 555–557; 73/293, 73, 170 R, 171, 40; 239/63; 250/227, 577, 573–574; 356/73.1; 137/558, 392; 350/96.23, 96.29–96.34

[56] References Cited

U.S. PATENT DOCUMENTS

| | | | |
|---|---|---|---|
| 3,045,223 | 7/1962 | Kapany et al. | 340/583 |
| 3,470,340 | 9/1969 | Hakka | 200/61.04 |
| 3,540,025 | 11/1970 | Levin et al. | 340/583 |
| 3,867,837 | 2/1975 | Malin | 73/73 |
| 4,159,420 | 6/1979 | Tsunoda | 250/227 |
| 4,256,403 | 3/1981 | Powell | 73/293 X |
| 4,266,878 | 5/1981 | Auer | 356/419 |
| 4,270,049 | 5/1981 | Tanaka et al. | 250/227 |
| 4,335,613 | 6/1982 | Luukkala | 73/599 |
| 4,379,289 | 4/1983 | Peek | 250/227 X |
| 4,468,567 | 8/1984 | Sasano et al. | 250/577 |
| 4,634,856 | 1/1987 | Kirkham | 250/227 |
| 4,689,484 | 8/1987 | McMahon | 250/227 |
| 4,812,014 | 3/1989 | Sawano et al. | 350/96.29 |
| 4,834,496 | 5/1989 | Blyler, Jr. et al. | 350/96.29 |
| 4,851,817 | 7/1989 | Brossia et al. | 340/583 |

Primary Examiner—Joseph A. Orsino
Assistant Examiner—Thomas J. Mullen, Jr.
Attorney, Agent, or Firm—Klaas & Law

[57] ABSTRACT

A system for automatic and real time detection of the presence or absence of a substance in an environment by monitoring variations in light energy transmitted through an optical fiber having a specially processed sensitive probe area. The sensitive probe area is positioned on, about or within the environment where a substance is to be detected. Because of differences in optical indices of refraction and energy absorption characteristics of different substances, the presence of different substances at the processed sensitive area will cause different proportional and characteristic attenuation of the light energy passing through the optical fiber. Changes in light energy transmission can be interpreted automatically to provide an indication of the condition of an environment.

18 Claims, 11 Drawing Sheets

FIBER OPTIC PROBE SYSTEM

FIELD OF INVENTION

This invention relates generally to apparatus and methods for detecting the presence and/or absence of a substances by use of light and fiber optic devices. The present invention relates particularly to detection of a substance such as water or petroleum liquids and/or a change in condition of a substance, such as change from water to ice. The present invention also relates generally to apparatus and methods for detection of liquids in the soil and more particularly, detection of liquid contaminant substances in the soil.

BACKGROUND AND SUMMARY OF INVENTION

This application is a continuation-in-part of prior copending U.S. application Ser. No. 838,283 filed Mar. 10, 1986, now U.S. Pat. No. 4,85 for Fiber Optic Probe System, the disclosure of which is incorporated herein by reference and the benefit of the filing date is claimed herefor.

In recent years efforts have been made to develop fiber optic technology for various purposes including the use of a bent fiber optic refractometer device for measurement of salinity in double diffusive thermohaline systems as described in Rev. Sci. Instrum. 56(2), February 1985 of the American Institute of Physics, the disclosure of which is incorporated herein by reference. Powell U.S. Pat. No. 4,256,403, the disclosure of which is incorporated herein by reference, discloses a water contaminate and fuel density detector using a longitudinally extending body of light transmitting material with light emitting means at one end to provide a group of divergent rays in angularly disposed light emission paths onto a plurality of vertically spaced light sensors for producing a signal corresponding to the index of refraction indicating the density of the fuel, while also indicating the presence of water in the fuel.

In general, the present invention utilizes a sheathed and/or coated optical fiber means having a first sheathed and/or coated light path portion connected to a light emitting device for transmitting light from the light emitting device along a first covered light transmission path, an intermediate, unsheathed, exposed core portion having an abraded peripheral surface for providing a sensor means, and a second sheathed and/or coated path portion connected to a light receiving device for receiving transmitted light from the light source and generating variable output signals dependent on characteristics of received light. The optical fiber device is constructed and arranged to prevent light loss in the first path portion and the second path portion with variable light losses occurring in the intermediate portion depending upon variations in environmental conditions at the intermediate portion. The variable light losses in the intermediate portion are dependent on the reflection and refraction and absorbtion characteristics of the intermediate portion of the optical fiber device and the reflection and refraction and absorption characteristics of the environmental medium in contact with the intermediate portion. Since various characteristics, such as reflection, refraction, heat of fusion, rate of temperature change in various phases, etc., of various mediums, such as air, water, ice, corn oil, gasoline, etc., are known or can be determined, the amount of light loss in the intermediate portion can be calculated with respect to various surrounding mediums. Differences in the amount of light received by the light measuring device can be used to indicate the nature or phase (i.e., solid, liquid, gaseous) of the environmental medium in contact with an outer surface of the intermediate portion of the optical fiber device.

Ice Detection

One form of the present invention provides an apparatus and methods for detecting the buildup of ice on surfaces, which apparatus and methods are capable of distinguishing between water and ice on the surface being observed, and for other purposes such as detecting the presence of water in gasoline or oil or level of liquids in a vessel. The detection of the buildup of ice on surfaces is provided by measurement of the difference between the light energy absorption and refractive indices of dissimilar materials using a sensor probe of special design. The system of the present invention provides for automatic and real time detection of water and icing on surfaces by monitoring variations in light energy transmitted through a bent optical fiber having a specially processed sensitive area at its bend. The sensitive area is preferably positioned adjacent, on, about or within the surface on which icing is to be detected. Because of differences in the optical indices of refraction and energy absorption characteristics of air, water and ice, the presence of one of these mediums on the surface of the optical fiber core at the processed sensitive area, will cause a proportional and characteristic attenuation of the light energy passing through the optical fiber. The resultant observed changes in light energy transmission can be interpreted mathematically to produce an indication of the presence of ice or other material on the surface being tested. A reference optical circuit may be used to provide compensation for variations in input energy levels, temperature, physical stress, ambient light, etc. Light energy of different wave lengths and energy levels may be used to compensate for or avoid interference with measurement that could be produced by differences in ambient lighting conditions or for the detection of other conditions and materials using the principle of characteristic absorption and resonance. The rate of ice accretion or precipitation may also be measured by the use of a capacitance system or an electrically conductive heater wire positioned on or about the sensitized area of the optical fiber.

Soil Moisture Detection

In many areas of the world, the availability of water and the cost of pumping irrigation water restricts crop production. One area where water conservation can be improved is in the efficient use of irrigation water. The ability to monitor the moisture content of the soil so that excessive irrigation can be prevented contributes to the efficient use of water resource.

The standard prior art technique for measuring soil moisture in the laboratory consists of sampling a given volume of soil from the field, weighing the sample and drying it. The dried sample is re-weighed. The weight loss occurred in the drying process represents the amount of water in the sample. The gravimetric soil moisture content is then calculated from the measured data.

Apparatus to determine moisture content in various bulk substances such as soil in the field have been available in different forms and with varying degree of success.

There are techniques that measure the matric potential of soil with a tensiometer. In this technique, a porous cup filled with water is buried in the soil. Water moves in and out of the cup in response to soil moisture content. A tube connects the cup to a vacuum gage or a manometer. The readings represent the soil matric potential. Tensiometer measurements are labor intensive, require frequent field readings and must be maintained with periodic additions of water.

There are devices that measure the ability of the soil to attenuate energetic radioactive particles such as neutrons or gamma ray and correlate such attenuation to the soil moisture content. Such a device is illustrated by U.S. Pat. to Morrison, No. 4,614,870. Systems incorporating such devices are generally of high cost and the attendant safeguards required in the handling of radioactive isotopes render such systems impractical for wide scale common application.

There are devices that measure the electrical impedance of the soil and impute the soil moisture content from the measured impedance. Such devices are illustrated by U.S. Pat. Nos. of Weintraub et al. 4,693,419; Iltis 4,483,904; Larson 4,531,087; Walsh 4,540,936; Mackay et al. 4,341,112; Hasenbeck 4,216,789 and Hasenbeck 4,137,931. These devices generally give poor results under high moisture condition. The soil salinity also affects the reading. Additionally, such devices have electrodes in intimate contact with the soil moisture; the long term reliability of the devices is severely affected by corrosion of the electrodes in the presence of soil moisture.

An object of the present invention is to provide reliable means for economically and accurately determining the soil moisture content and continuously monitor the moisture content in the soil such as under an agricultural field, and thus, when preselected moisture content is detected, with appropriate signal processing at the system controller, provide control to the release of shutoff of irrigation water. The present invention is directed to an apparatus capable of detecting the moisture content of bulk substances such as soil that overcomes disadvantages of prior art techniques.

In general, the soil moisture sensor of the present invention utilizes an optical path sensor such as a fiber optic means having a continuous fiber optic light path connected to a light source means for transmitting light from the light source means along the light path, through a sensor portion in the light path having a treated sensitive peripheral surface, and the other end of said light path connected to a light detector means for receiving transmitted light from the light source and generating output signals dependent on the characteristics of received light. The optical sensor device is constructed and arranged such that variable light losses occur in the said sensor portion depending upon the presence of sensed medium in the environment where the sensor portion is located. The variable light losses in the sensor portion are dependent on the amount of sensed medium in contact with the sensor portion. For example, in the soil moisture content detection apparatus, the sensor portion is buried in soil at a desired depth, the sensed medium is water in the soil, various soil moisture content in the soil allows varying amounts of water to be in contact of the sensor portion surface. The water adsorbed and absorbed by the sensor portion causes different amount of light loss at the said sensor portion. Difference in the amount of light received by the light detector means can be used to indicate the difference in moisture content of the soil in contact with the sensor portion of the apparatus. The light source means and light detector means of the apparatus are electrically connected to a sensor control circuit means. Power required by the light source means and light detector means is provided by the sensor control circuit means; and the light detector signal output is processed by the sensor control circuit means and is interfaced to conventional alarm system power shutoff, machine controller and the like to control the flow of irrigation water.

The present invention provides an apparatus and method for detecting the moisture content of bulk substances such as soil. The apparatus of the present invention provides for automatic and real time detection of moisture content of the soil in which the optical path sensor portion of the apparatus is buried, by monitoring the variation in light energy transmitted through a continuous optical path such as a length of optical fiber having a specially processed sensor portion in the length. Various moisture content in the soil allows different amounts of water in the soil to contact the sensor portion. The moisture adsorbed and absorbed by the sensor portion causes attenuation of the light energy passing through the optical path. The resultant observed change in light energy transmission can be processed to produce a signal indicative of relative moisture content of the soil. When the signal reaches a predetermined reference value, a control valve is energized or de-energized to provide control of flow of irrigation water.

UNDERGROUND TANK LEAK DETECTION

This invention also relates generally to apparatus and method for detecting the presence of liquid contaminant substances in the soil. More particularly, the present invention relates to the apparatus and method for the detection of soil contamination by petroleum products such as gasoline, jet fuel, heating oil, etc. near underground storage tanks.

Leaking of underground storage tanks and their associated piping is a major source of environmental contamination. Product loss from such leaks may cause adverse effects on the environment, endanger lives, reduce income and require great expenditures for clean up. The are approximately three and a half million underground storage tanks in the U.S. It is estimated that 15% of the tanks are leaking into the surrounding soil. The risk of ground water contamination, already extreme, is likely to increase with the aging of the ever greater number of the underground tank population The majority of underground tanks are for gasoline storage associated with retail sales.

An objective of the invention is to provide means for economically and accurately determining the presence of petroleum contamination in the soil near underground petroleum storage tanks and to provide warning when such leakage is detected. There are several prior art techniques commonly practiced for the detection of leaking underground storage tanks. The most common of which has to do with determining the physical integrity of the storage tanks. One of such techniques is the volumetric leak detection test. Volumetric leak detection tests identify a leaking tank and determine the leak rate based on the measurement of the liquid level of a full tank. The change in liquid volume due to leakage can be determined by measuring parameters associated with the volume change; including changes in liquid level, temperature, pressure and density of the stored liquid. Such tests are generally labor intensive and require long testing time. Another one of such techniques is by the measurement of the ability of a tank system to maintain pressure. A tank and piping system is pressurized and the pressure of the system is monitored. An unexpected pressure loss of the system indicates a leak in the system. This technique is illustrated by U.S. Pat. of Zuehlsdorf No. 4,496,077.

There are devices that are located in wells next to underground storage tanks that contain sensors that detect the effect of leakage of underground tanks. The sensors incorporate substances that chemically react with the leaked contaminants and the resulting physical change of the substances cause electrical contacts to be made or broken thus generating an electrical signal. For example, substances that dissolve in gasoline such as styrene-butadiene rubber, polystyrene, polyisoprene, etc. are incorporated in gasoline leakage sensors. When such sensor is in contact with gasoline and or gasoline vapor, electrical switches normally held open or shut by the polymer member is allowed to shut or open respectively due to the dissolution and thus weakening of the polymer member. This technique is illustrated by U.S. Pat. of Hakka, No. 3,470,340.

The present underground tank leak detection apparatus of the invention provides an apparatus capable of detecting the presence of liquid petroleum contaminants such as gasoline, jet fuel, diesel fuel, etc., in bulk substances such as soil that overcomes disadvantages of prior art techniques. The tank leak detection apparatus utilizes an optical path such as a fiber optic means having a continuous fiber optic light path connected to a light source means for transmitting light from the light source means along the optical fiber light path, through a sensor portion in said light path having a treated sensitive peripheral surface, and the other end of said light path connected to a light detector means for receiving transmitted light from the light source and generating output signals dependent on the characteristics of received light. The optical path device is constructed and arranged such that variable light losses occur in the said sensor portion depending upon the presence of sensed medium in the environment where the sensor portion is located. The variable light losses in the sensor portion are dependent on the amount of sensed medium in contact with the sensor portion. For example, in a gasoline soil contamination detection apparatus, the sensor portion is buried in soil at a desired depth, near an underground gasoline storage tank to be monitored, the sensed medium is gasoline which is adsorbed in the soil in the event the underground tank leaks, various degrees of leakage of the tank allows varying amounts of gasoline into the soil thus allowing varied amounts of gasoline to contact the sensor portion. Gasoline adsorbed and absorbed by the sensor portion causes different amount of light loss at the said sensor portion. Difference in the amount of light received by the light detector means can be used to indicate the detection of gasoline in the soil contacting the sensor portion of the apparatus. The light source means and light detector means of the apparatus are electrically connected to a sensor control circuit means. Power required by the light source means and light detector means is provided by the sensor control circuit means; and the light detector signal output is processed by the sensor control circuit means and is interfaced to conventional alarm system, power shut-off, machine controller and the like to provide warning and or to initiate other desired appropriate actions.

The apparatus of the present invention provides for automatic and real time detection of petroleum contamination of the soil in which the sensor portion of the light path of the apparatus is buried, by monitoring the variation in light energy transmitted through a continuous light path having a specially processed sensor portion in the path. Various amounts of contaminant present in the soil allows different amounts of contaminant in the soil to contact the sensor portion. The different amounts of contaminant adsorbed and absorbed by the sensor portion cause a proportional attenuation of the light energy passing through the optical path. The resultant observed changes in light energy transmission can be processed to produce a signal indicative of relative degree of contamination of the soil. When the signal reaches a predetermined reference value, an alarm system is energized to provide warning about the presence of contaminant in the soil.

Fluid Level Sensor

The present invention also relates generally to apparatus and method for detection of the level of liquid in a contained area. More particularly, the present invention relates to an apparatus and method for the detection of liquid level in a tank for the purpose of controlling process pumps or inventory control. More particularly, the present invention relates to the detection of the level of flammable and explosive liquids where sensing means which have the potential to spark an explosion can not be used.

In many industrial processes, the amount of liquid medium accumulated in a storage or process vessel is an important process variable. Knowledge of the liquid inventory therein present allows better operation of the process. Liquid level information may be a process parameter necessary for the actuation of pumps, heaters and other common process equipment. The ability to monitor liquid levels accurately allows the efficient operation of a process and contributes to the quality of typical industrial products.

The standard prior art method of manually sensing levels in storage vessels and reservoirs consists of stick, hook and tape gages in open vessels where the surface of the liquid may be readily observed. The stick gage is a suitably divided typically vertical rod, or stick, anchored in the vessel so that the magnitude of the rise and fall of the liquid level may be observed directly The hook gage provides a needle point, which is adjusted to produce a very tiny pimple in the liquid surface at the level reading, thereby reducing the meniscus error. The tape gage reads the correct elevation when the point of a bob just touches a liquid surface.

Many forms of glass sight gages are available for measurement of liquid level. Liquid in a tank or vessel is connected to the sight gage glass by suitable fitting, and when the tank is under pressure, the top of the gage must be connected to the tank vapor space. Thus liquid rises to substantially the same height in the sight glass as in the tank and liquid level is measured by a suitable scale.

Various types of float mechanism are used for liquid level measurement. The float, tape and pulley gage are examples of float gages.

The changes in buoyancy of a solid as its immersion in a liquid is varied can also be used to measure liquid level when the densities of the liquid and vapor are essentially constant with changing liquid level. Changes in the temperature of the liquid or vapor typically affect their densities introducing inaccuracies.

Hydrostatic head may also be used to measure the level of liquid in a tank or vessel. The pressure exerted by a column of liquid varies directly with its density and height and thus may be used to measure liquid levels if the density is known and constant during the period of measurement. Temperature compensation is often included because of density changes related to temperature.

Electrode systems may be constructed wherein the conductivity between two or more electrodes is monitored and a change therein is imputed to mean a change in the level of the sensed liquid. Such systems typically require the liquid to be electrically conductive and may require a conduction voltage large enough to be hazardous in an explosive vapor environment.

Capacitance measuring devices can also be used to measure liquid levels. If the sensed liquid is a dielectric, one or two conductive rods are placed in the tank or vessel, extending nearly to the bottom. If the sensed liquid is an electrical conductor, only one rod is needed and it must be electrically insulated from the sensed liquid.

Nuclear level gages are used for special applications. Typically these are a source of gamma radiation separated from a gamma ray detector by an intermediate vessel in which the liquid level varies and is sensed by attenuation of the gamma radiation.

Sonic level sensors have been built based on the time of flight of a pulse of acoustic energy to travel from the sonic source to the liquid surface and return by reflection at the liquid vapor interface to a sonic receiver.

Optical fibers with a U-bend have been used to detect index of refraction. Because the index of refraction of a liquid is different than that of air, a change in the index of refraction can signal the change in position of a liquid/air interface. An example of this is the use of a bent optical fiber refractometer as a single position liquid level sensor. The design has been commercially applied to monitoring the liquid level in storage tanks. An optical fiber with a series of bends, with radius of curvature decreasing with each bend has been described as a refractometric fluid level sensor by M. A. Belkerdid et al. (M. A. Belkerdid, N. Ghandeharioun and B. Brennan, Fiber Optic Fluid Level Sensor, SPIE Volume 566, Fiber Optic and Laser Sensor III (1985), 153-158. Because light is emitted along the entire length of the fiber by the constantly decreasing radius of curvature, liquid levels could be sensed in a continuous way.

An object of the present invention is to provide reliable means for economically and accurately determining the level of liquid in a tank or vessel and to continuously monitor the change of liquid level in a tank or vessel and thus, with appropriate signal process, provide control to the actuation of pumps, valves, heaters and other process equipment.

The present fluid level sensor invention is directed to an apparatus capable of automatically detecting the level of a medium such as petroleum products in a containment vessel that overcomes disadvantages of the prior art techniques. In general, the present invention uses a fiber optic means having the fiber optic light path connected to a light emitting device for transmitting light from the light emitting device along the optical fiber light path, through the fiber optic portion having a striated or abraded peripheral surface for providing a sensor portion means, and the other end of said light path connected to a light receiving device for receiving transmitted light from the light source and generating output signals dependent on the characteristics of received light. The optical fiber device is constructed and arranged with variable light losses occurring in the said sensor portion or portions depending upon variations in the environmental conditions at the sensor portion or portions The variable light losses in the sensor portion or portions are dependent on the environmental medium in contact with the sensor portion. When the aforementioned medium containment vessel contains varying amounts of medium, under the influence of gravity the depth of medium with respect to the bottom of the containment vessel will vary, increasing in depth with an increase in the amount of medium present in the containment vessel. If the fiber optic means of the present invention is arranged vertically in the containment vessel, the depth and change in depth of medium in the containment vessel may be sensed by the number and position of sensor portions in contact with the medium. The presence of the medium at the sensor portion changes the amount of light losses in that sensor portion. This in turn causes varying amounts of light to be conducted by the fiber light conducting means having a sensor portion or portions to the light receiving and signal producing device. Variation in the amount of sensor portion surface area in contact with the medium causes corresponding variation in the amount of light lost by the fiber light conducting means containing a sensor portion or portions in contact with the sensed medium. The amount of light received by the light receiving and signal producing means can be used to indicate the amount of medium present in a containment vessel.

The present invention provides an apparatus and method for detecting the amount of medium in a containment vessel and the rate of change in the amount of medium in a containment vessel. A difference in the amount of light received by the light receiving device over time can be used to indicate a change in the amount of medium within a corresponding time within the containment vessel which allows the rate of change with time or flow rate of medium into or out of the containment vessel to be calculated by conventional algorithms which use tank cross sectional area and change in medium level in the mathematical derivation of flow rate. To be able to sense the rate of change in height of the medium within a containment vessel is useful for a number of process control purposes and also for the detection of leakage of the stored medium from or infiltration of a second medium or mediums into the containment vessel.

BRIEF DESCRIPTION OF THE DRAWINGS

Illustrative and preferred embodiments of the invention are shown in the accompanying drawings wherein.

DETAILED DESCRIPTION

Figure 1:
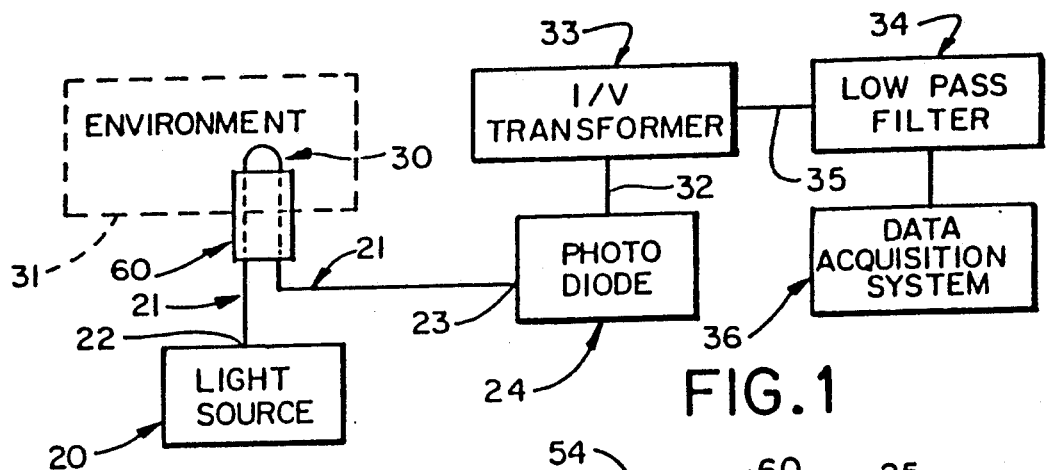
FIG. 1 is a schematic block diagram of a condition detection system of the present invention.
Figure 2:
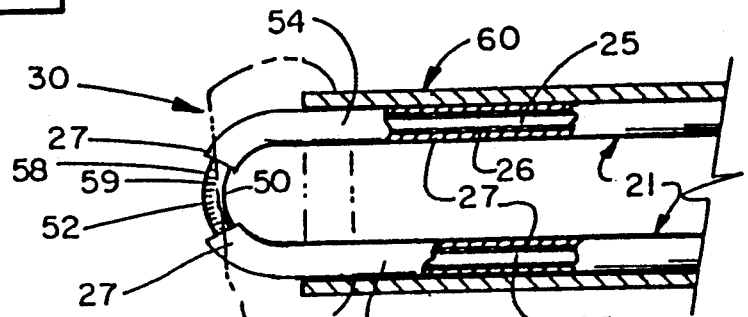
FIG. 2 is a partial cross-sectional view of a sensor element according to the present invention.

In general, as shown in FIGS. 1 and 2, the present invention employs a light source means 20, such as a conventional infrared light emitter device (LED) for continuously or intermittently generating light when connected to a power supply. A fiber optical cable means 21 is connected at one end portion 22 to the light source means 20 for continuously transmitting light beams along the fiber optical cable means to an end portion 23 connected to conventional light receiving and signal generating detector means 24, such as conventional infrared light receiving device (LRD), for generating variable output signals which vary in accordance with the amount of light transmitted thereto. The fiber optical cable means 21 is of conventional design, except as modified as hereinafter described, and comprises one or more core fibers 25 having a generally cylindrical outer peripheral surface configuration. The entire outer surface of the core fiber or fibers is conventionally covered by an optical coating or cladding material 26 which prevents lateral transmission of light while enabling only longitudinal transmission of light. A protective sheath 27 is usually provided circumjacent the coated core fiber or fibers. A condition sensing probe means 30 is operably associated with the fiber optical cable means to provide a section in the light transmission path wherein the amount and intensity of light travelling through the fiber optical cable means 21 to the associated detector means 24 is varied in accordance with a change in condition of a sensed medium in an environment 31 associated with the condition sensing probe means 30 whereby an output signal from detector means 24 on an output line 32 is varied in accordance with a change in condition of the sensed medium. The detector output signal may be transmitted to a conventional I/V transformer means 33 which transmits a corresponding signal to a conventional low pass filter means 34 through a line 35 and then to a conventional data acquisition system means 36 whereat changes in the output signal are utilized to determine changes in and state of condition of the medium.

Figure 3:
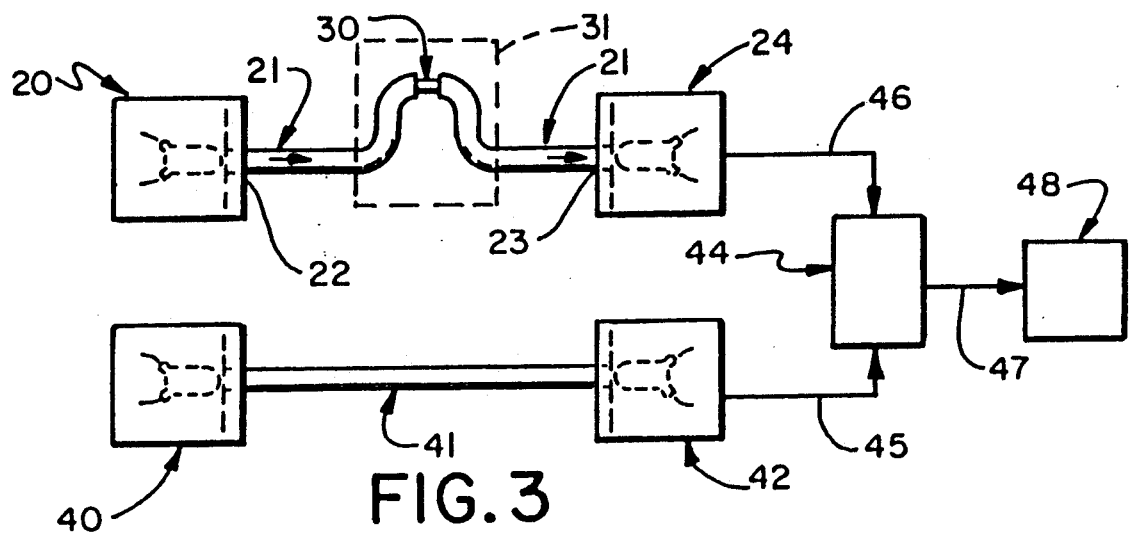
FIG. 3 is a schematic block diagram of a presently preferred embodiment of a condition detection system of the present invention.

In one embodiment, as shown in FIG. 3, a reference signal generating means is employed which comprises a light source means 40, a fiber optical cable means 41, and a light receiving and signal generating detector means 42, all of the same type as previously described, but which may or may not include a sensor probe means 30 or other reference condition indicating means. A reference output signal generated by reference signal light detector means 42 and the condition signal generated by condition sensing detector means 24 are transmitted to a conventional electronic controller means 44 via lines 45, 46 for comparison of the signals and for generation of a control signal on line 47 representative of the change in condition at sensor means 34. The control signal is transmitted to a conventional control output means 48 such as an Apple-type personal computer for providing a visual or audible indication of the change in or condition of the medium.

The sensor probe means 30 comprises a portion of the fiber optical cable means 21 from which the sheathing material 27 and the coating material have been removed to provide an exposed medium contact area in which the core fiber or fibers have no sheathing nor coating precluding transfer of a portion of the light therethrough. The exposed medium contact area is preferably formed at an U-shaped loop section 50, as shown in FIG. 2, of the fiber optical cable means which has a curved portion 52 and parallel side portions 54, 56. An outermost surface 58 on curved portion 52 is provided with transverse striations 59 thereacross which may be formed during removal of the coating material by lightly sanding the peripheral surface of the core fiber or fibers with abrading material such as a piece of sandpaper, preferably 600 grit silicon carbide, or the like. The U-shaped loop section 50 may be mounted in a support means, such as a cylindrical tubular member 60, with a protecting, sealing and retention means, such as an adhesive sealing material 62, associated therewith. Support means 60 is mounted in a suitable manner on or in support structure, such as an airplane, runway, engine, refrigerator, etc., so as to locate the sensing area in the environment where the change of condition is to be sensed.

Figure 9:
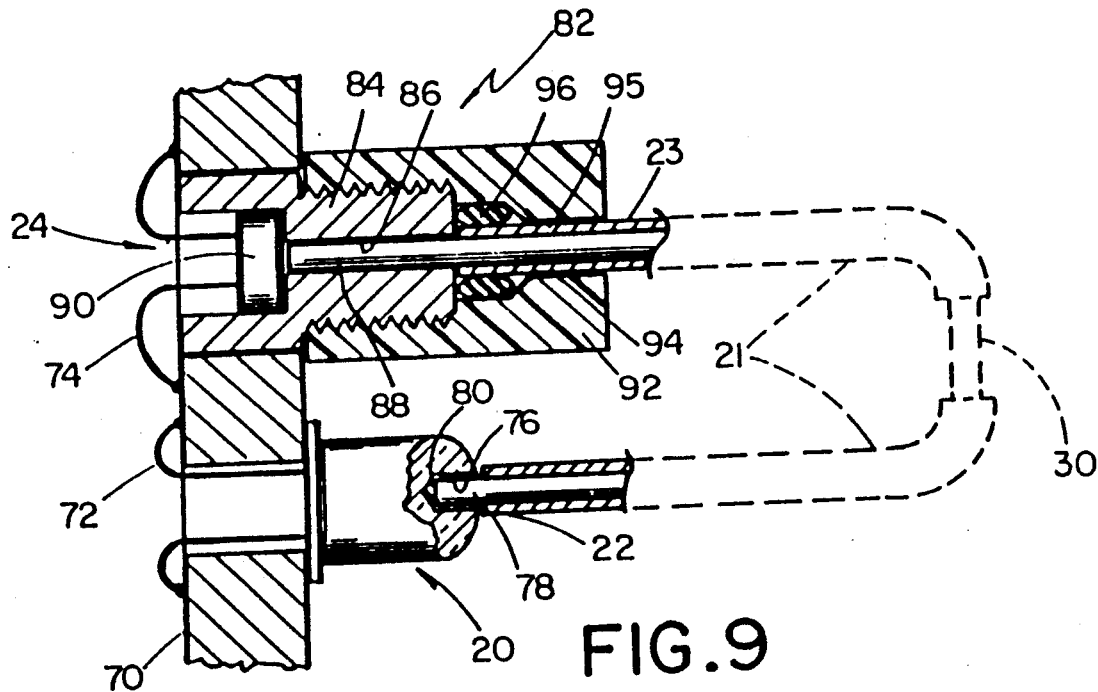
FIG. 9 is a partial cross-sectional view of a probe assembly.

FIG. 9 shows an assembly wherein the emitter means 20 and the detector means 24 are mounted on a printed circuit board 70 with leads 72, 74 connected thereto in a conventional manner. End portion 22 of optical fiber means 22 is connected to emitter means 20 by drilling a hole 76 in the end of the emitter means to receive core end portion 78 which is secured therein by a conventional optical grade adhesive material 80. Optical fiber end portion 23 is connected to detector means 24 by a conventional coupling means 82 comprising a threaded plug member 84 having a central bore 86 to receive and hold unsheathed core end portion 88 in face to face contact with the detector plate 90. A threaded cap member 92 has a central bore 94 to receive sheathed optical fiber portion 95 and a compressible retaining ring means 96.

The fiber optical cable means is preferably a conventional PVC sheathed fiber optical light transmitting device made of polystyrene or acrylic or polymethyl methacrylate polymer fiber core section having a diameter of one millimeter such as Model No. P1000 of General Fiber Optics Co. A sensor area is made by removing approximately two and ½ inches of the sheathing and also removing approximately 5/8 to 11/16 of the cladding and/or coating material centrally of the non-sheathed area. The entire circumference of the outer surface of the exposed section of the polymer fiber core is abraded by lightly sanding with a piece of 600 grit silicon carbide sandpaper by movement of the sandpaper around the peripheral surface transversely to the longitudinal axis of the polymer fiber to produce a roughened surface with circumferentially extending striations along the exposed section of the polymer fiber core to produce a cylindrical surface sensor area therealong. Good results are obtained when the sanded area produces between approximately 50 to 70 percent light attenuation in air and approximately 60 percent attenuation is preferred. It has been discovered that unsatisfactory results are obtained without sanding the exposed section and also, if the sanding occurs parallel to the central longitudinal axis, rather than laterally thereof. Then, the fiber optic device may be bent at the sensor area to provide a loop having a radius of approximately 9/16 inch to provide an U-shaped probe portion. However, it has been discovered that the sensor area will operate satisfactorily in a straight line condition or a partially curved condition. A conventional 100 mA P-N gallium aluminum arsenide 880 nanometer infrared light emitting device, TIL906-1 available from Radio Shack, or MFOE71 manufactured by Motorola Corporation, and a conventional photo darlington-type light activated receiving and signal generating device, MFOD73, manufactured by Motorola Corporation, are fixedly sealably associated with and connected to opposite end portions of the fiber optic device in closed light transmitting and receiving relationship therewith.

The attenuation of light propagating through a treated optical fiber has been investigated and repeatable experiments have demonstrated that the light passing through the fiber is increasingly attenuated when air, ice and liquid water, respectively, are present on the treated portion of the fiber probe. The results of experiments indicate a variation in the attenuation of the light passing through a treated portion of a fiber depending upon the amount of abrasion. The result suggests there is a strong correlation between the rate of change in the attenuation of the light passing through the fiber and the degree of surface abrasion and number of the grooves as well as the total abraded area. Other experimental results provide evidence on the effect of the nature of the surface grooves in the observed phenomenon. Fibers that were treated by sanding parallel to the axis of the fiber showed a less-pronounced effect.

An experimental model was developed as the result of electron micrograph studies. Electron micrographs of the treated fibers indicate the surface morphology of the fiber can be approximated by a geometry similar to that diagrammed in FIG. 10. Since the geometry appears to be somewhat similar to a thread configuration, we contemplate that a thread cutting or an ion beam milling technique may be employed to cheaply, reliably and reproducibly provide the required sensor surface configuration.

Figure 10:
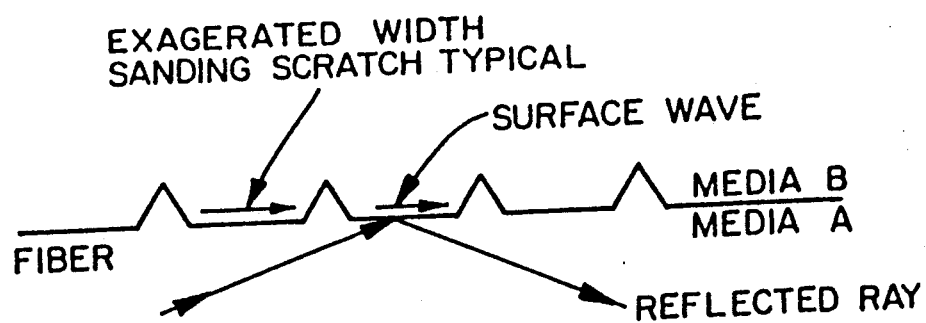
FIG. 10 is a schematic representation of a probe surface.

Most of the light propagating through the fiber is totally internally reflected off the inner surface of the fiber. The phenomenon of total internal reflection was observed centuries ago and is adequately described within the framework of classical electromagnetic theory. When light is totally internally reflected off a boundary separating medias A and B, there exists a surface electromagnetic wave that propagates parallel to boundary (FIG. 10). The electromagnetic fields of the wave, the evanescent fields, are attenuated at an exponential rate into media B.

The surface wave, produced by total internal reflection, will be located within approximately one-half micron or less, from the outer surface of the fiber at the bottom of the groove so as to fully interact with the surface incongruities of the treated fiber. Electron micrographs of the treated fibers indicate the surface irregularities are on the order of ten microns or more in height and substantially greater than the location of the surface wave. Thus, the evanescent fields of the electromagnetic surface wave go to zero well under the height of the surface incongruities and the surface wave strongly interacts with the surface morphology created by the fiber treatment.

When a surface wave encounters an obstruction, a portion of the wave is transmitted back into the fiber. A mathematical model of the interaction of the evanescent fields and the surface topography of a treated fiber has been constructed. The model assumed liquid water, ice or air on the fiber surface and computed the relative intensity of the light transmitted through the fiber. The results predict the light propagating through the fiber should be attenuated least when air is in contact with the fiber surface, a bit more for ice and most for liquid water. The results are in accordance with all the observed experimental results described previously.

An investigation of the physical principles involved to understand the observed phenomenon has been conducted. A number of experiments indicate the sanding treatment of the optical fiber significantly enhances the observed effect. A mathematical model has been constructed that assumes the basis for the effect is the interaction of the evanescent fields of a surface electromagnetic wave with the irregular surface topography of the treated fiber. The model predicts results that are in accordance with the observed experimental results. Thus, mathematical models may be developed for various environments, mediums and apparatus which would treat the fiber as an electromagnetic wave-guide with an accurate numerical description of the surface irregularities.

Since light that is refracted back into the fiber is sensed by the photodetector attached to the end of the fiber light path, absorption characteristics are important. In testing for water and ice, the sensing fiber has been found to be most sensitive when the energy input is above nominally 500 nanometers wavelength. Tests have shown that emitters with nominal output of 880 nanometers produce good results. The wavelength is outside the visible spectrum in what is referred to as near infrared. We believe that longer wavelength emitter and detector pairs would be more sensitive.

The reason for the increased sensitivity when using the longer wavelength emitters is related to the absorption characteristics of water. The relationship between absorption characteristics and wavelength for water are known. One of the conclusions that may be drawn from this information is that 880 nm wavelength energy is absorbed at rate approximately 6000 times greater than 490 nm wavelength energy. This absorption characteristic is true for liquid water as well as ice and humid air. We have demonstrated in our experimentation the ability to reliably sense the relative humidity of an air sample with exactly the same apparatus used to detect the presence of ice and water.

Our conclusion is that sensitivity to a given medium can be enhanced by selection of an emitter having an output wavelength that is strongly absorbed by the sensed medium. In one experiment, we used a fiber sensor using a dual wavelength output emitter (565 nm and 695 nm). It is conceivable that the concept of multiple as above or continuously variable wavelengths (using a tuneable laser for example) could be used to construct a multiple media sensing device for the detection of media having discrete multiple absorption wavelength bands.

In operation, the LED and the LRD are connected to suitable low DC voltage (e.g., 1.5 volt) power supply circuits which may be battery operated. The LRD output circuit is connected through suitable intermediate circuitry to data acquisition means such as an IBM PC-XT computer with ASYST programming and a Keithly Series 500 system for data acquisition and plotting. Measurements are then made under normal operating conditions with the sensor area exposed to air to establish normal standard voltage output of the LRD (e.g., 1.5 to 2 volts) in an air environment. Then, the probe area is subjected to a water environment so that the exterior surface of the probe area is in intimate surface contact with water. Measurements are then made to establish a normal standard voltage output of the LRD in a water environment which will be substantially different (e.g., a thirty percent shift) than the normal standard voltage output of the LRD for an air environment. Measurements are then made to establish a normal standard voltage output of the LRD in an ice environment which will also be significantly and measurably different (e.g., a downward five to fifteen percent shift) from the voltage output of the LRD for the water environment. These measurements may be utilized to establish reliable air-water-ice indicator signal calibration standards to cause visual and/or audible indications of conditions at the sensor area. In order to provide more reliability at lower cost, a reference signal system comprising a fiber optic cable device and associated LED and LRD and circuitry is employed as shown in FIG. 3. The reference signal fiber optic cable device is identical in construction, size, arrangement and location to the condition sensing cable device except that the reference signal fiber optic cable device may or may not have a sensor area or other reference condition indicating means. Thus, the reference signal system is subject to substantially the same environmental and operating conditions as the condition sensing system whereby the effect of ambient light, length, curves, bends, temperature, humidity, etc. variations can be taken into account in processing the condition sensing output signal to establish the presence of water or ice at the sensing area. Preferably, a single light source is used so that both cable devices receive light from the same source.

In operation of the system of FIG. 3, light signals are received by photodetectors 24 and 42 through fibers 21 and 41, respectively. Signal strengths detected by the detectors are compared in a controller circuit 44. The strength of the signals is monitored for changes which indicate there is water or ice at the sensing site. Tests have shown that a thirty percent signal strength shift indicates there is water at the sensing section 30 of fiber 21 and a subsequent signal strength shift further indicates that water is freezing on the sensing section These signal shifts may be used to cause the output device 48 to be activated in an appropriate manner such as providing a warning light or alarm.

Figure 4:
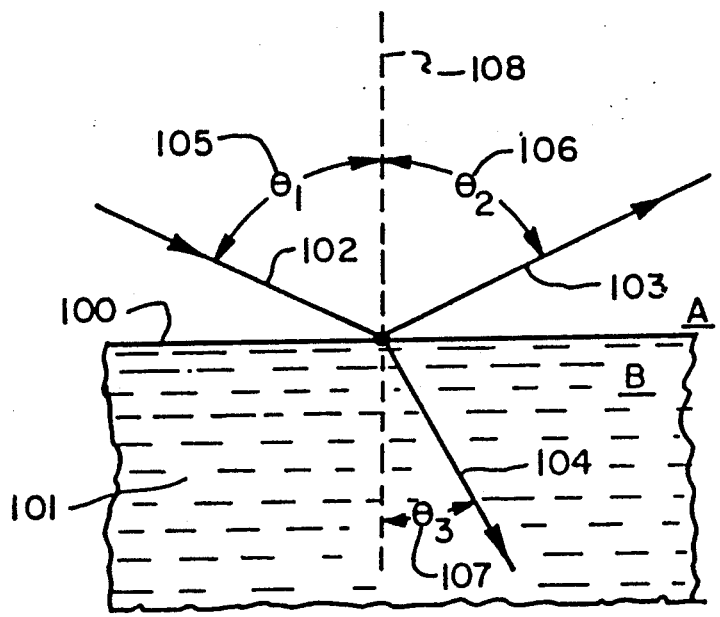
FIG. 4 is a diagrammatic illustration of the optical properties of light incident upon a transparent or translucent layer.

The aforedescribed apparatus and methods for detecting changes in conditions of a medium are based in part upon the use of the differences between refractive indices of different materials. Index of refraction of different materials is a measure of the ratio of the phase velocity of light in a vacuum to that in the predetermined material. FIG. 4 diagrammatically illustrates that a light beam falling upon a transparent or translucent medium surface 100 is both reflected from the surface and bent or refracted as it enters the medium 101. The incident light beam is represented in FIG. 4 by a single line, the incident ray 102, parallel to the direction of propagation. The reflected and refracted beams are also represented by rays 103 and 104, respectively. The angle of incidence 105, angle of reflection 106, and angle of refraction 107 are measured between the normal to the surface 108 and the appropriate ray as shown in the figure. The physical laws governing reflection and refraction are as follows:

For reflection: $O_1 = O_2$

For refraction: $\dfrac{\sin O_1}{\sin O_3} = n_{21}$ where $n_{21}$ is a constant called the index of refraction of medium B with respect to medium A. The index of refraction of water with respect to a vacuum is 1.333. The index of refraction of ice with respect to a vacuum is 1.309. The index of refraction of air with respect to a vacuum is 1.0002.

Figure 5:
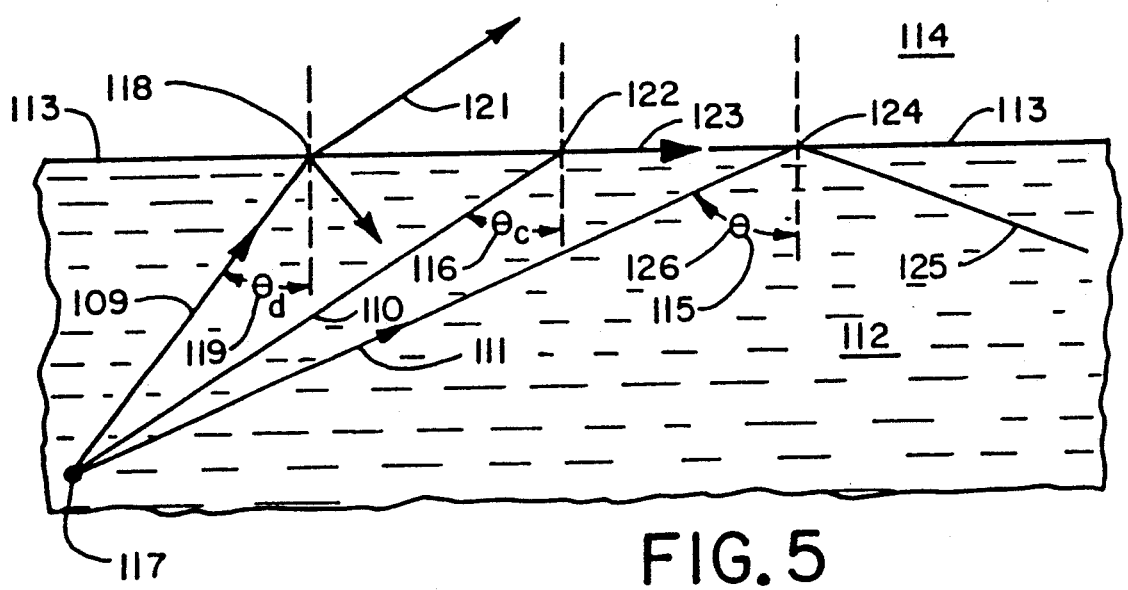
FIG. 5 is a diagrammatic illustration of the internal reflections within a transparent or translucent layer.

The present invention utilizes this difference in refractive index along with absorption characteristics to detect, and therefore, distinguish between the presence of air, water and ice using the principal and techniques of fiber optic refractometry. FIG. 5 illustrates the physical phenomenon called total internal reflection. Total internal reflection is a phenomenon in which electromagnetic radiation 109, 110, 111 in a given medium 112 which is incident on the boundary 113 with a less-dense medium 114 having a lower index of refraction at an angle 115 greater than the critical angle 116 is completely reflected from the boundary interface 113 between the dense medium 112 and less-dense medium 114. To illustrate, ray 109 from point source 117 is incident at 118 on the medium boundary 113. Because angle 119 is less than angle 116, ray 109 is both reflected along ray line 120 and refracted along ray line 121. Ray 110 from point source 117 is incident on the medium boundary 113 at point 122. Because the angle of incidence 116 is equal to the critical angle, the total ray is reflected along ray 123 coincident with the boundary 113. Ray 111 from point source 117 is incident on the medium boundary 113 at point 124. Because the angle of incidence 126 of ray 111 is greater than the critical angle 126, the ray 111 is totally reflected within the dense medium 112 along ray 125.

If we let $n_{112}$ be the refractive index relative to vacuum of the material 112, and if $n_{114}$ is the refractive index relative to vacuum of the material 114, then R1 is the ratio of these indices as follows:

$$R_1 = \dfrac{n_{112}}{n_{114}}$$

The critical angle 116 and the amount of light transmitted through the interface 113 varies with $R_1$ as described by the Fresnel equations. For an internal reflection ($R_1$ greater than 1) and a constant angle of incidence 119, the amount of light transmitted through the interface 113 along ray 121 increases as $R_1$ decreases. As the amount of light transmitted through interface 113 increases along ray 121, the amount of light reflected internally along ray 120 decreases. For an internal reflection ($R_1$ greater than 1) and a constant angle of incidence 119, the amount of light transmitted through the interface 113 along ray 121 decreases as $R_1$ increases resulting in an increase in the amount of light reflected internally along ray 120. Hence, measurement of the amount of light reflected internally 120 or refracted externally 121 to the dense medium 112 may be used to determine $R_1$. If the index of refraction of either the dense or less dense medium is known, the other may be calculated from the relationship stated previously.

Ice Detection

Figure 6:
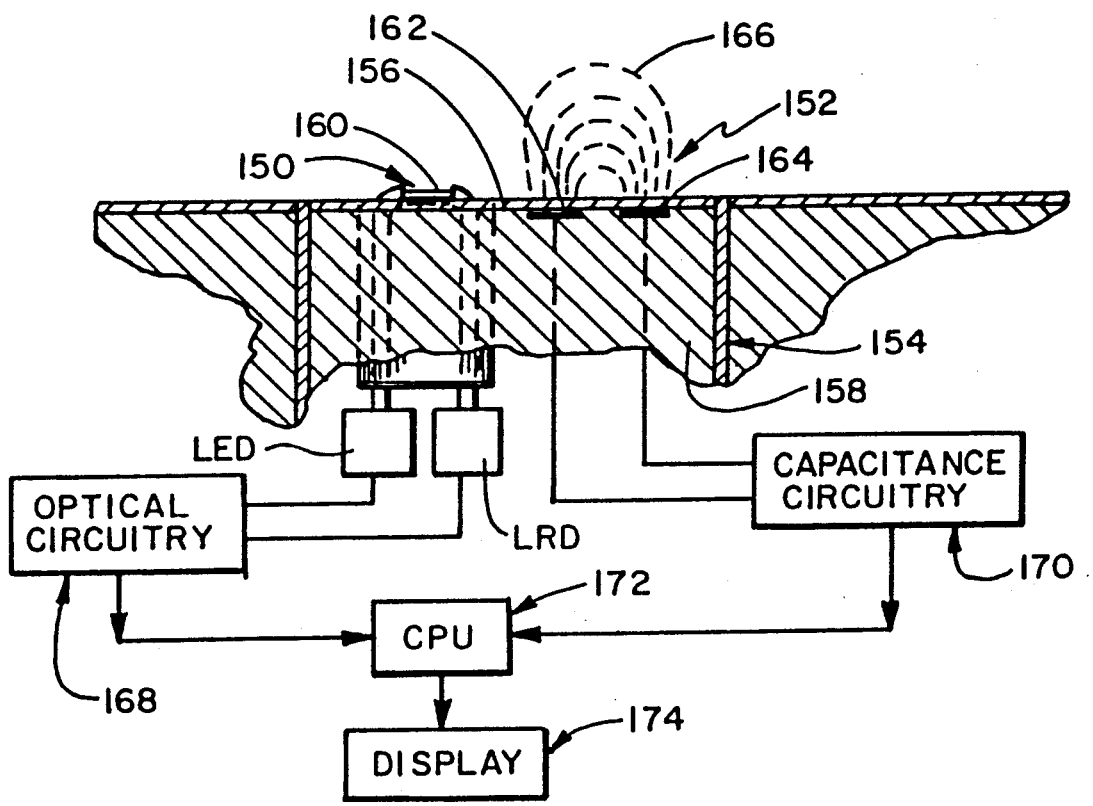
FIG. 6 is a schematic block diagram of a presently preferred embodiment of an ice presence and ice accretion rate sensing system.

FIG. 6 shows a system for detection of the presence of ice and the rate of accretion (buildup) of ice. A bent optical fiber ice presence detection probe means 150, of the type shown in FIGS. 1 and 2, and ice accretion measuring probe means 152 are mounted in juxtaposition to one another in support means 154 including a suitable outer surface 156 covering a body of suitable electrically insulating material 158. The curved portion 160 of the probe means 150 extends above surface 156 for exposure to the environment. Electrodes 162, 164 are located beneath and closely adjacent surface 156 so as to create an electrical field 166 therebetween which extends above surface 156. Thus, the formation of ice on the curved portion 160 of optical fiber probe means 150 provides an ice presence signal from an optometric output means 168 as previously described. The formation of ice on surface 156 above the electrodes 162, 164 interrupts the electrical field 166 and a conventional capacitance measuring circuit means 170 may be used to measure variations in the electrical field. The amount of variation in the electrical field will be proportional to the thickness of the ice on cover surface 156 so that the rate of ice accretion can be determined by correlation between time and thickness in a conventional controller means 172 having a clock circuit and receiving thickness output signals from circuit means 170 as well as ice presence output signals from optometric output means 168. A conventional computer means 174 with a visual display receives output signals from controller means 172 by which ice warning and accretion rate information may be displayed and/or utilized to generate audible and/or visual warning signals. A system of this type is particularly adapted for use at airport runways and vehicle roadways. For such usage, the probe support material 158 and cover surface material 156 preferably correspond to materials used for the runway and/or roadway so as to simulate actual conditions on and in the runway and/or roadway.

Figure 7:
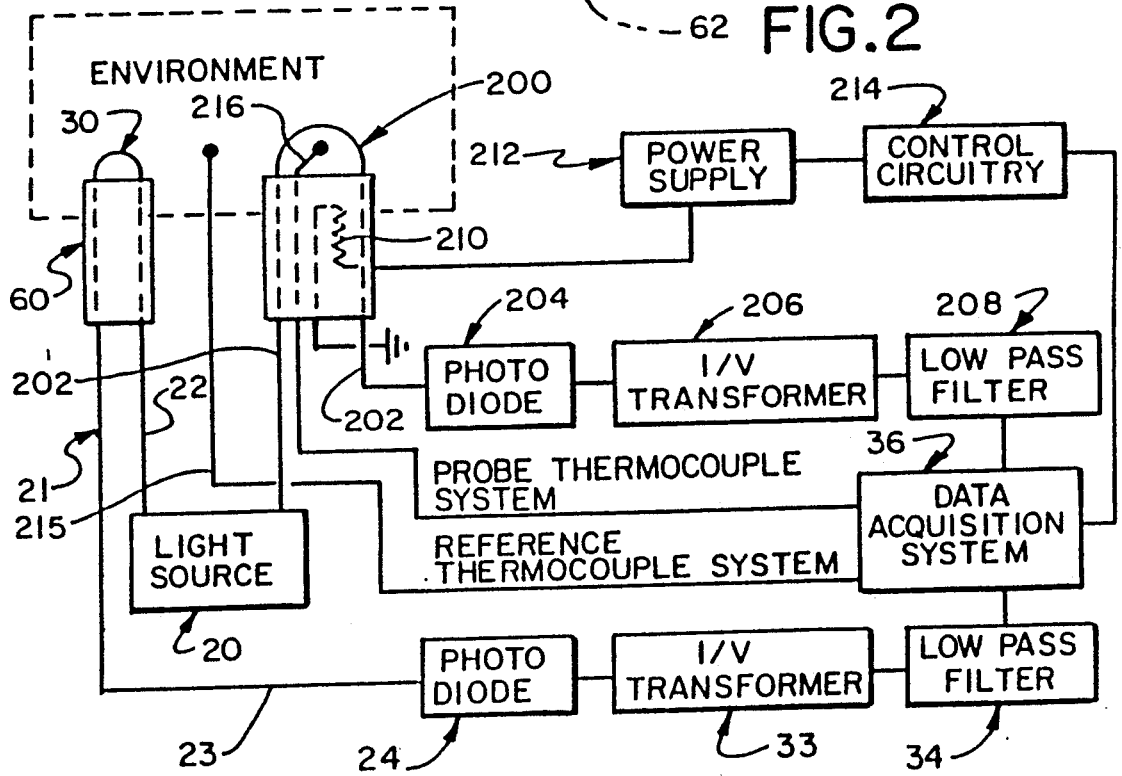
FIG. 7 is a schematic block diagram of an alternative embodiment of an ice presence and ice accretion rate sensing system of the present invention.
Figure 8:
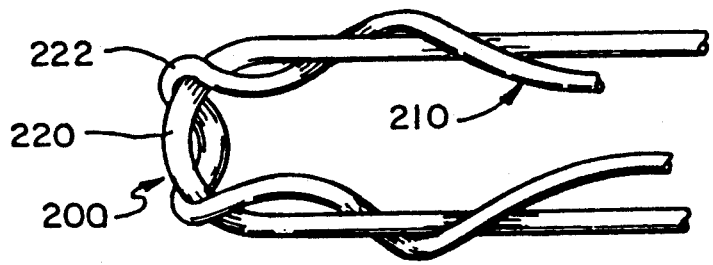
FIG. 8 is a partially broken view of another embodiment of a sensor element according to the present invention.

An alternative embodiment of the invention for the detection of the presence of ice and for obtaining an indication of the thickness of the ice at the site and for determining the rate of accretion or buildup of the ice at the site is shown in FIGS. 7 and 8. Referring to FIG. 7, a first probe 30 is constructed and operates the same as the probe shown in FIGS. 1 and 2. The fiber optic conduit 21 is connected to a light source 20, which may be a conventional laser device, and the intensity of the light from the light source is measured by a photo diode 24 in the same manner as previously described. In this embodiment a second probe 200 of generally similar design is provided which is constructed from a fiber optic conduit 202 which is connected to light source means 20 for receiving light therefrom and to a photo diode detection means 204 and associated transformer circuitry means 206, low pass filter means 208 connected to data acquisition means 36 in the same manner as probe 30. In addition to the foregoing, the probe 200 is provided with a heater means 210 connected to suitable heater circuit means 212 including control circuit means 214 which will energize the heater 210 as soon as any ice is detected on the probe 200 by means of a detected change in the measured light intensity by photo diode 204 and the associated circuitry until the ice is melted and then de-energize the heater until ice again forms on the probe. Thermocouple circuits 215, 216, and a feedback circuit (not shown) are provided to measure the amount of energy being provided to the heater 210 which is a function of the ice accretion rate so that the amount of energy required to repeatedly de-ice the probe 200 and the time required during the period of time that ice is detected on the probe 200 can be used to provide a real time reading of both the ice accretion rate and its thickness. The probe 200 with heater element 210 may be constructed as shown in more detail in FIG. 8 wherein the fiber optic light conduit 220 is wrapped with a resistance heating element 222, such as 0.005 inch diameter Nichrome wire, in the manner shown to optimize the heat transfer to the interface between the probe and the ice at the test site. Icing indication causes the controller to turn on heater 210 which melts the ice formed on the sensing section 200. At indication of water (when the heater melts the ice), the controller shuts the heater off until ice is again sensed. The cycling of the heater is thus repeated during the climatic episode. The controller monitors the power consumed per fixed time interval by the heater. The quantity of power so dissipated is proportional to the ice accretion rate, e.g., the output device could be a watt meter and be calibrated to read inches of ice per minute. The thermocouples 215, 216 allow the controller to have a reference temperature input for calibration purposes. Combining the icing detection device 30 and the icing accretion rate detection device 200 in close proximity allows the detection of the onset, accretion rate and the dissolution of icing at the sensor areas of the instruments.

The system of FIG. 7 detects ice accumulation as a function of the cumulative energy required to remove the ice from the probe tip 200. The operation of this system is as follows: (a) Ice forms on a probe tip and is detected; (b) after a short time delay, an electric current is allowed to pass through resistance element 210 associated with the fiber optic structure; (c) as thermal energy is conducted to the probe tip, ice melts off. The refractometer circuitry 204, 206, 208 detects the change from ice to water. The electric current is interrupted to allow the ice forming cycle to repeat; (d) by signal processing, the electrical energy is summed to yield the power consumed in melting the ice accumulated in the combined time period of initial delay and power application. A combination of factors including energy consumption and time, together with the physical constants related to ice, water and air temperature can be used to calculate ice accumulation per unit of time. The process described in steps (a)-(d) are repeated automatically each time ice is detected as it forms on the probe tip. The total ice accumulation will be the summation of ice accumulation measured during each cycle. The total dissolution of icing is detected by a second reference, non-heated refractometer probe 30 which also indicates the beginning of icing.

The foregoing apparatus and methods provide a system for detection of presence of water and ice and a change of phase of water to ice in the atmosphere by use of fiber optical tube means having an elongated passage therewithin with a first inlet end portion for receiving a beam of light and a second outlet end portion for discharging the beam of light. An intermediate portion of the fiber optical tube means has a specially processed exterior surface providing a light transmission opening means for enabling passage of a portion of the light beam therethrough. Light measuring means are connected to the outlet portion of the fiber optical tube means for measuring the amount of light transmitted thereto and for generating signals indicative of the amount of light received thereby. Mounting means mount the intermediate portion of the fiber optical tube means on a structure having at least one surface exposed to the atmosphere and locate the light transmission opening means in juxtaposition to the surface with the exterior surface of light transmission opening means being located in the atmosphere and being subject to the same atmospheric conditions as the surface. The exterior surface is constructed and arranged to enable accumulation and retention of water thereon for changing the amount of light transmitted through the light transmission opening means and the amount of light transmitted to the light measuring means. A condition indicating means is connected to the light measuring means for indicating the presence of ice on the exterior surface of the light transmission opening means. The exterior surface of the light transmission opening means has a coefficient of friction and surface tension characteristics such as to cause water and ice to adhere thereto. The tubular light transmitting means has an exterior non-translucent covering for defining a substantially closed central cylindrical light path between a light inlet opening and a light outlet opening wherein the amount and intensity of light contained therein is transmitted from the light inlet opening to the light outlet opening without substantial reduction in amount and intensity of light. A selected portion of the exterior covering at a selected portion of the tubular light transmitting means is removed to provide a non-covered section whereat light transmitting surface geometry is substantially different than in the other portions of the tubular light transmitting means. In one embodiment utilizing a U-bend, the selected portion of the tubular light transmitting means is located at an angle of inclination relative to the light inlet opening so as to cause the light to impinge on the selected area at an angle of incidence and reflection whereby a sensed medium material on the non-covered section will cause a detectable difference in the index of refraction and reflection absorption of the light at the non-covered section depending upon the type and condition of the sensed medium material. A mounting means is provided for mounting the light transmitting means in a manner in which the non-covered section is exposed to various having various indices of refraction and reflection causes varying exit conditions of the light beam at the light outlet means. The detector means receive output signals from the light receiving means and generate a control signal indicative of the change in condition on the exterior surface of the selected area of the light transmission means. The exterior detection portion of the light transmitting means has an abraded, non-smooth surface with striations extending transversely to the axis of the light beam and being exposed to the variable external conditions for surface contact by adhesion with and/or immersion in fluids surrounding the exterior portion.

DESCRIPTION OF THE ALTERNATIVE EMBODIMENTS

Figure 11:
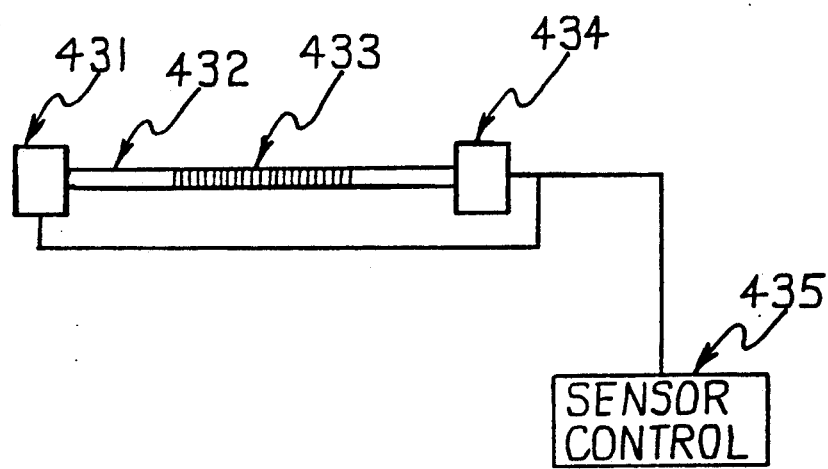
FIG. 11 is a pictorial representation of the side view of the optical path sensor apparatus.

In general, FIG. 11 shows apparatus for detecting a sensed medium which comprises a light source means 431, such as a conventional infrared light emitting diode (LED) for generating light when connected to a power supply. An optical path of transparent material such as glass, nylon, polymethylmethacrylate, polystyrene, 2-hydroxyethyl methacrylate, etc. The optical path 432 could be in the form of an optical fiber connected at one end to the light source means 431 for transmitting light beams along the fiber optic cable means to the other end of the fiber optic cable means which is connected to conventional light receiving and signal generating detector means 434, such as conventional light receiving device (LRD), for generating variable output signals which vary in accordance with the amount of light transmitted thereto. Alternatively, the optical path could be provided by molding the transparent material in an elongated shape bridging the light source means 431 and light detector means 434 at each end of the molding. The sensor apparatus is electrically connected to the sensor control 435. Power required by the light source means 431 and light detector means 434 is provided by the sensor control 435; and the light detector signal output is processed by the sensor control 435 and is interfaced to conventional alarm system, power shut-off, machine controller and the like. The optical path means 432 allows longitudinal transmission of light along the axis between the light source means 431 and light detector means 434. A sensor portion 433 is operably associated with the optical path means to provide a section in the light transmission path wherein the amount of light traveling through the path means is varied when the sensed medium in the environment is in contact with the sensor portion 433 whereby an output signal from detector means 434 is varied with the detection of the sensed medium. The sensor portion 433 is a section of the optical path means exposing a peripheral surface area to the sensed medium The peripheral surface area of the sensor portion 433 may be increased by transverse striations on the surface of the optical path material. This may be formed by abrading the peripheral surface of the optical path material, in a transverse direction, with abrading material such as sandpaper and the like. Alternatively, such transverse striations may be obtained by cutting shallow grooves with a pointed cutting tool on the outermost surface of the optical path means. For example, such striations may be cut at 0.2 mm apart with a 60 degree cutter to a depth of 0.2 mm.

The aforedescribed apparatus and method for detecting the sensed medium is based upon light energy attenuation of the optical path sensor caused by the differences of refractive indices, light absorbance and reflectance of different sensed media in contact with, thus adsorbed and absorbed by, the optical path material.

SOIL MOISTURE DETECTOR

Figure 12:
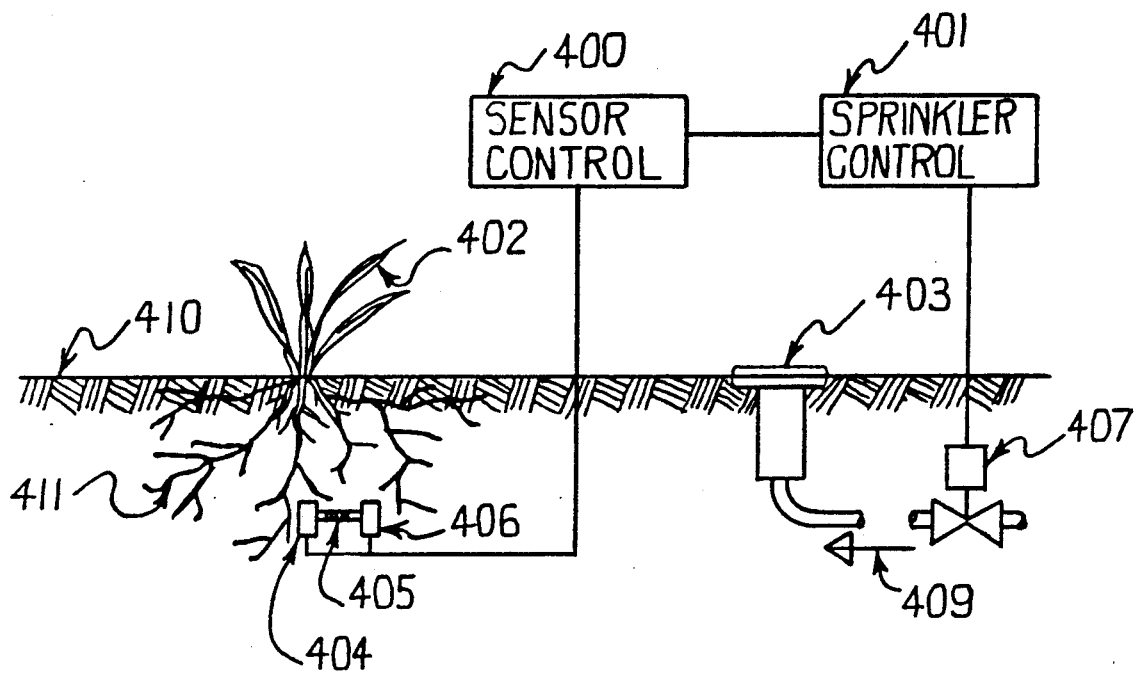
FIG. 12 is a pictorial representation of a sprinkler control system utilizing a moisture content sensor apparatus constructed in accordance with the teachings of the present invention.

In the embodiment illustrated in FIG. 12, the aforedescribed sensor apparatus is used as a soil moisture detector. The sensed medium is water that is present in the soil circumjacent to the optical path sensor means. Referring to FIG. 12, the sensor apparatus as aforedescribed comprising light source means 404, optical path means 405 and light detection and signal generating means 406 is buried in the soil at a depth near the root zone of plants such as grass and the like. The sensor apparatus is electrically connected to the sensor control 400. Power required by the light source means 404 and light detector means 406 is provided by the sensor control 400; and the light detector signal output is processed by the sensor control 400 and is interfaced to a conventional sprinkler controller. Varying amount of water in the soil circumjacent to the optical path sensor portion 405 cause varying amount of water to be adsorbed and absorbed by the sensor portion thus attenuating the amount of light transmitted through the optical path sensor portion and cause varying amount of light to reach the light detector means 406 thus cause a varying signal level to be generated by the detector means 406. This signal is outputted to the sensor control 400. Upon a preselected signal level from the light detector means 406, corresponding to a preselected soil moisture content circumjacent to the optical path sensor means 405, the sensor control 400 processes the detector output and issues signal to a conventional sprinkler controller 401 to inhibit the irrigation water flow 409 by closing the sprinkler solenoid valve 407. Alternatively, upon a preselected signal level from the light detector means 406, corresponding to a preselected soil moisture content circumjacent to the optical path sensor means 405, the sensor control 400 processes the detector output and issues signal to a conventional sprinkler controller 401 to enable the irrigation water flow 409 by opening sprinkler solenoid valve 407 causing water to be discharged through sprinkler head means 403.

UNDERGROUND STORAGE TANK DETECTOR

Figure 13:
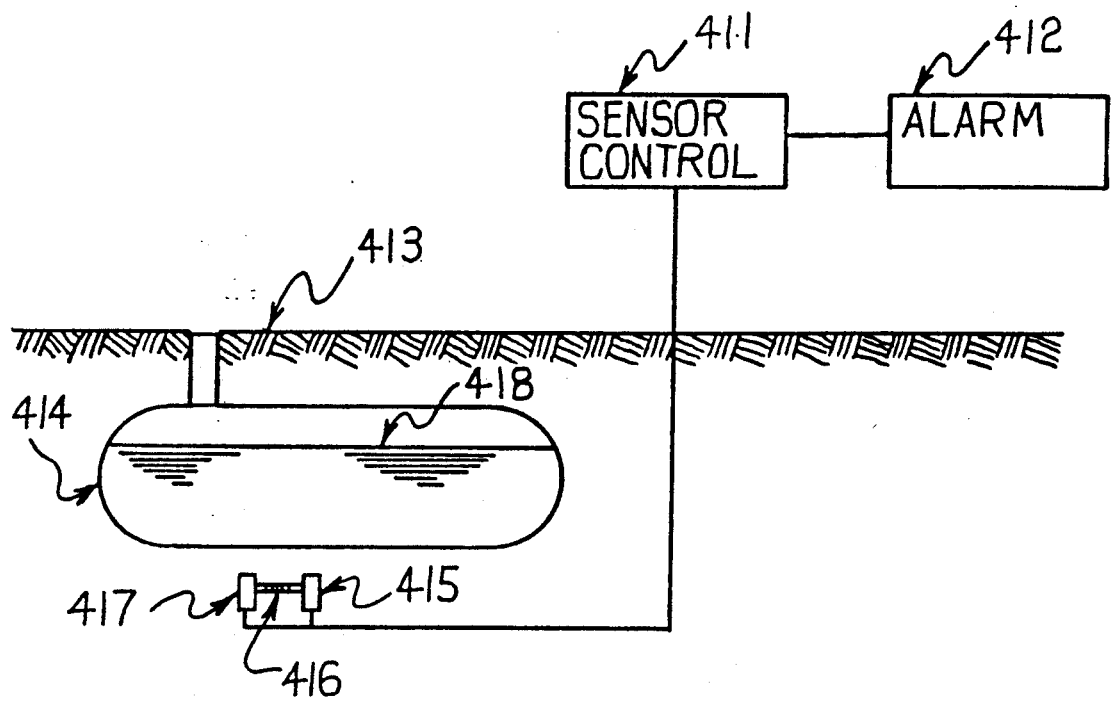
FIG. 13 is a pictorial representation of an underground tank being monitored for leaks originating from the tank utilizing sensor apparatus constructed in accordance with the teachings of the present invention.

In the embodiment illustrated in FIG. 13, the aforedescribed sensor apparatus comprising light source means 417, optical path sensor means 416 and light detector and signal generating means 415 is used as a soil contamination detector when installed in the soil near underground storage tank 414. The sensor apparatus is electrically connected to the sensor control 411. Power required by the light source means 417 and light detector means 415 is provided by the sensor control 411; and the light detector signal output is processed by the sensor control 411 and interfaced to conventional alarm system, power shut-off, machine controller and the like. In the event of leakage of the underground tank 414, petroleum product 418, stored in the tank, such as gasoline, jet fuel, diesel fuel, etc., will flow into the bulk filler material surrounding the tank such as gravel soil etc. The sensed medium is leaked petroleum products present in the gravel or soil circumjacent to the optical path sensor means 416. The presence of such petroleum product circumjacent to the optical path sensor means 416 produces a signal level change from the light detector and signal generating means 415. This change in signal level is outputted to the sensor control 411. Upon a preselected signal level change from the light detector means 415, corresponding to signal level caused by contacting the petroleum product, the sensor control 411 issues a signal to activate a conventional alarm system 412. The alarm indication signified detection of petroleum product by the sensor apparatus in the soil or gravel near the underground tank; thus provide warning that the tank is leaking.

Figure 14:
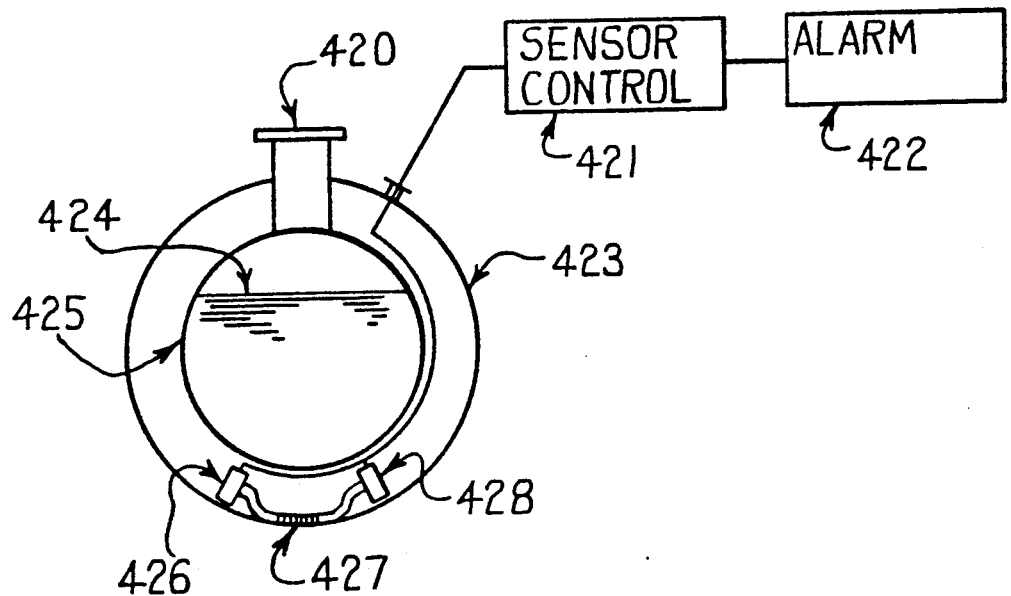
FIG. 14 is an end sectional view of a double wall storage tank. The cavity between the outer wall an inner wall is being monitored for leaks utilizing sensor apparatus constructed in accordance with the teachings of the present invention.

In the embodiment of FIG. 14, the aforedescribed sensor apparatus comprising light source means 426, optical path sensor means 427 and light detector and signal generating means 428 is used as a leakage detector located in the annular space between the outer and inner walls of a double wall storage tank 423 and is located in such a fashion that liquid present in this space will contact the optical path sensor means 427. For example, the sensor portion may be located at the lowermost portion of the annular space between the outer and inner walls of the double wall tank. The sensor apparatus is electrically connected to the sensor control 421. Power required by the light source means 426 and light detector means 428 is provided by the sensor control 421; and the light detector signal output is processed by the sensor control 421 and interfaced to conventional alarm systems, power shut-offs, machine controllers and the like. The primary sensed medium is the petroleum product stored in the inner tank, such as gasoline, jet fuel, diesel fuel, etc. In the event of an inner tank leakage, the leaked petroleum product comes in contact with the optical path sensor means 427 of the sensor apparatus. The presence of such petroleum product circumjacent to the optical path sensor means 427 produces a signal level change, corresponding to the signal level caused by contacting the petroleum product, from the light detector and signal generating means 428. This change in signal level is outputted to the sensor control 421. Upon receiving a preselected signal level corresponding to the petroleum product presence signal level from the light detector means 428, the sensor control 421 issues a signal to activate a conventional audio and or visual alarm system 422. The alarm indication signifies detection of petroleum product by the sensor apparatus in the annular space between the two walls of the tank; thus providing warning that the inner tank is leaking. It was experimentally determined that the signal level produced when the sensor means 427 contacts petroleum distillates is distinct to the signal level of that in contact with water. Thus the sensor apparatus can detect the presence of either petroleum or water in the annular space by outputting distinctive signal levels. Therefore alternatively, upon receiving a preselected signal level corresponding to the water signal level, the sensor control 421 issues a signal to activate another alarm on the alarm system 422. This alarm indication signifies detection of water by the sensor apparatus; thus provide warning that the outer tank wall is leaking and water, possibly ground water, is entering the annular space of the double wall tank.

Figure 15:
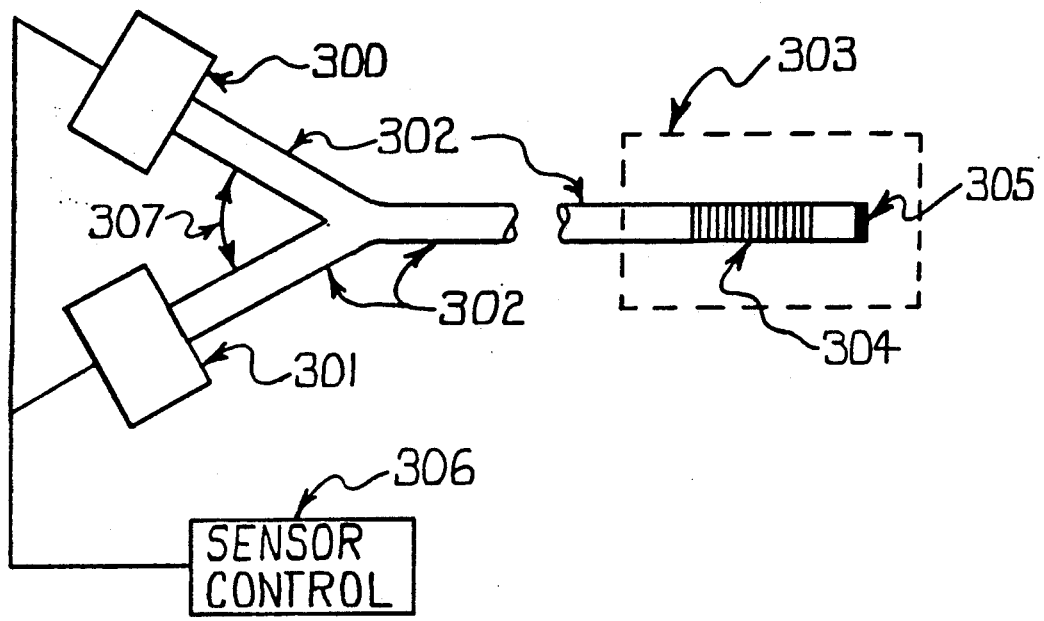
FIG. 15 is a representation of an alternate configuration of the optical path sensor apparatus where the sensor portion is located, at opposite end of the light source and light detector means.

FIG. 15 shows another optical path sensor apparatus comprising a fiber optic cable means 302 joined in a conventional manner into a "Y" shape. Two of the legs of the fiber optic cable means subtend an angle 307 less than 90 degrees; these two legs are connected one to the light source means 300 and the other to the light detector and signal generating means 301. The third leg of the fiber optic cable means contains the sensor portion 304 and the end of the fiber optic means is polished and coated with a reflective coating 305. The light source means 300, such as a conventional infrared light emitting diode (LED) for generating light when powered, is connected to the fiber optic cable means 302 for transmitting light along the fiber optic cable means to the reflective coating 305 at the far end of the fiber optic cable means 302. The light receiving and signal generating detector means 301, such as conventional light receiving device (LRD), for generating variable output signals which vary in accordance with the amount of light transmitted thereto, is connected to the fiber optic cable means 302 so that a portion of the light reflected by the mirrored end of the fiber optic cable means 302 is received by the light detector and signal generating means 301. The sensor apparatus is electrically connected to the sensor control 306. Power required by the light source means 300 and light detector means 301 is provided by the sensor control 306; and the light detector signal output is processed by the sensor control 306 and is interfaced to alarm systems, power shut-offs, machine controllers and the like. The fiber optic cable means 302 is of conventional design, except as modified as herein described, and comprises one or more core fibers having a generally cylindrical outer peripheral surface configuration. The entire outer surface of the optical fiber or fibers is conventionally covered by an optical coating or cladding material which prevents lateral transmission of light while enabling only longitudinal transmission of light. An optical path sensor portion 304 is operably associated with the fiber optic cable means to provide a section in the light transmission path wherein the amount of light traveling through the fiber optic cable means is varied in accordance with the detection of or change in condition of the sensed medium in an environment 303 associated with the sensor portion 304 whereby an output signal from detector means 301 is varied in accordance with the adsorption and absorption by the sensor portion 304 of the sensed medium. The sensor portion 304 is a section of the fiber optic means where the coating or cladding has been removed to provide an exposed peripheral area to be in contact with the sensed medium. Alternatively, the optical path 302 could be provided by molding transparent material in an elongated shape bridging the light source means 301, light detector means 301 and the reflective tip 305 at each end of the molding. The peripheral surface area of the sensor portion 304 may be increased by transverse striations which may be formed by sanding the peripheral surface of the core fiber or fibers, in a transverse direction, with abrading material such as sandpaper and the like. Such transverse striations may also be obtained by rotating a pointed cutting tool around the outermost surface of the optical fiber means. For example, such striations may be cut at 0.2 mm apart with a 60 degree cutter to a depth of 0.2 mm.

Figure 19:
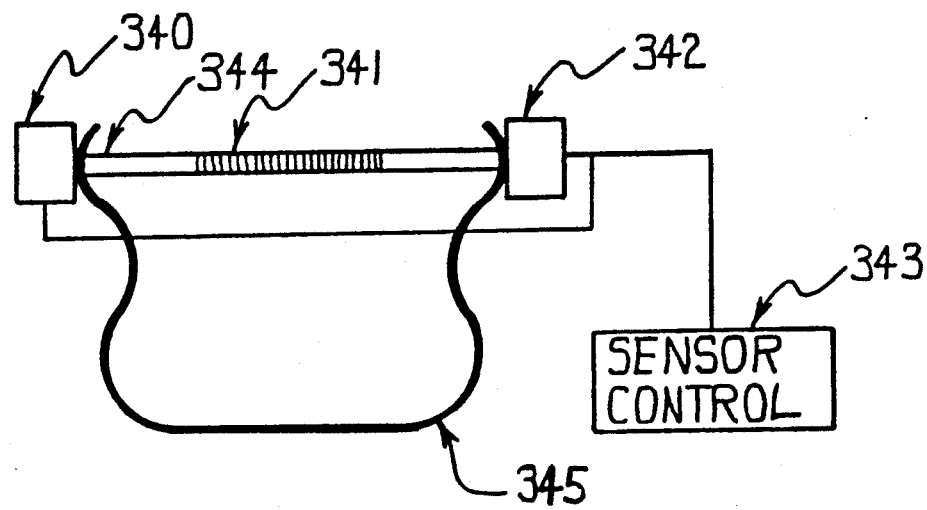
FIG. 19 is a representation of an alternate configuration of the optical path sensor apparatus where the optical path material is subjected to a tensile loading by a spring device.

FIG. 19 shows another sensor apparatus with a light source means 340, such as a conventional infrared light emitting diode (LED) for generating light when connected to a power supply. An optical path such as fiber optic cable means 344 is connected at one end to the light source means 340 for transmitting light beams along the optical path means 344 to the other end of the optical path means 344 which is connected to conventional light receiving and signal generating detector means 342, such as conventional light receiving device (LRD), for generating variable output signals which vary in accordance with the amount of light transmitted thereto. A spring means 345 is installed contacting both ends of the fiber optic cable means 344 such that the fiber optic cable means is subjected to tension by the spring device means 345. The sensor apparatus is electrically connected to the sensor control 343. Power required by the light source means 340 and light detector means 342 is provided by the sensor control 343; and the light detector signal output is processed by the sensor control 343. The fiber optic cable means 344 is of conventional design and comprises one or more core fibers having a generally cylindrical outer peripheral surface configuration. An optical path sensor portion 341 is operably associated with the optical path means 344 to provide a section in the light transmission path wherein the amount of light traveling through the fiber optic cable means is varied in accordance with the detection of or change in condition of the sensed medium in an environment circumjacent to the sensor portion 341 whereby an output signal from detector means 342 is varied in accordance with the adsorption and absorption by the sensor portion 341 of the sensed medium. The sensor portion 341 is a section of the optical path means where the coating or cladding has been removed to provide an exposed peripheral area to be in contact with the sensed medium. Alternatively, the optical path 344 could be provided by molding the transparent material in an elongated shape bridging the light source means 340 and light detector means 342 at each end of the molding. The peripheral surface area of the sensor portion 341 may be increased by transverse striations which may be formed by sanding the peripheral surface of the core fiber or fibers, in a transverse direction, with abrading material such as sandpaper and the like. Such transverse striations may also be obtained by rotating a pointed cutting tool around the outermost surface of the optical fiber means. For example, such striations may be cut at 0.2 mm apart with a 60 degree cutter to a depth of 0.2 mm. In the event the sensed medium chemically attacks the optical path means 344, such attack alters the physical as well as the optical property of the fiber optic cable means 344, a change in light transmission ability of the fiber from the light source means 340 to the light detector means 342 will result; if the optical path material 344 is weakened by the attack, the spring means 345 elongates the optical path means 344 by stretching it. This causes signal level change from the light detector means 342. This change is outputted to the sensor control 343 and is processed to interface with alarm systems, power shut-offs, machine controllers and the like. For example, polystyrene optical fiber core is chemically attacked by petroleum distillates such as gasoline, jet fuel, diesel fuel, etc. Therefore, for example, the herein described sensor apparatus, when employing a polystyrene optical fiber, and is in contact with gasoline, will change optical property and physically weaken and elongate or break under the tension of the spring means 345. This changes the amount of light transmitted from the light source means 340 to the light detector means 342 and causes a change in the light detector 342 signal level. This change is outputted to the sensor control 343 and is processed to interface with alarm systems, power shut-offs, machine controllers and the like.

Figure 17:
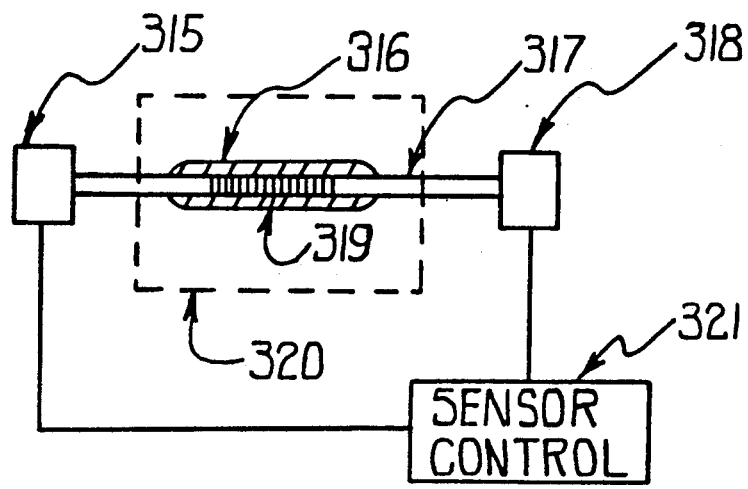
FIG. 17 is a representation of an alternate configuration of the optical path sensor apparatus where the sensor portion is covered by a substance that is selectively permeable to desired analytes.

FIG. 17 shows a sensor apparatus comprising a light source means 315, such as a conventional infrared light emitting diode (LED) for generating light when connected to a power supply. An optical path means 317 is connected at one end to the light source means 315 for transmitting light beams along the optical path means to the other end of the optical path means 317 which is connected to conventional light receiving and signal generating detector means 318, such as conventional light receiving device (LRD), for generating variable output signals which vary in accordance with the amount of light transmitted thereto. An optical path sensor portion 319 is operably associated with the optical path means 317 to provide a section in the light transmission path wherein the amount of light traveling through the optical light path means is varied in accordance with the detection of the sensed medium in an environment circumjacent to the sensor portion 319 whereby an output signal from detector means 318 is varied in accordance with the adsorption and absorption by the sensor portion 319 of the sensed medium The sensor portion 319 is a section of the optical path means where the coating or cladding has been removed to provide an exposed peripheral area to be in contact with the sensed medium. Alternatively, the optical path 317 could be provided by molding the transparent material in an elongated shape bridging the light source means 315 and light detector means 318 at each end of the molding. The peripheral surface area of the sensor portion 319 may be increased by transverse striations which may be formed by sanding the peripheral surface of the core fiber or fibers, in a transverse direction, with abrading material such as sandpaper and the like. Such transverse striations may also be obtained by rotating a pointed cutting tool around the outermost surface of the optical fiber means. For example, such striations may be cut at 0.2 mm apart with a 60 degree cutter to a depth of 0.2 mm. A covering means 316 is applied over the sensor portion 319, and is of a substance that is selectively dissolvable or permeable to a desired medium. For example, the covering means 316 may be a substance that is dissolvable by petroleum fuels and is not affected by water such as natural rubber. Therefore the herein described sensor apparatus, with this covering, may be immersed in a water tank without causing the sensor portion 319 to be in contact with the water due to the rubber covering; however, if petroleum fuels is introduced into the tank, the covering dissolves allowing water to penetrate to the sensor portion 319 causing a signal level change by the light detection means 318 to the sensor control 321, which processes the signal to indicate presence of petroleum in the water tank. This signal is then interfaced with conventional alarm systems, power shut-offs, machine controllers and the like. In another example, the covering means 316 may be of a substance that is not permeable to petroleum fuels and is only permeable by water, such as polytetrafluoroethylene sulfonate. Therefore the herein described sensor apparatus, with this covering may be immersed in a petroleum fuel tank without causing the sensor portion 319 to be in contact with the fuels due to the barrier properties of the covering; however, if water is introduced into the tank, the permeable coating 316 allows the water to penetrate and contact the sensor portion 319 causing a signal level change to be outputted by the light detector means 318 to the sensor control 321, which processes the signal to indicate presence of water in the petroleum tank. This signal is then interfaced with conventional alarm systems, power shut-offs, machine controllers and the like.

Figures 18, 18A:
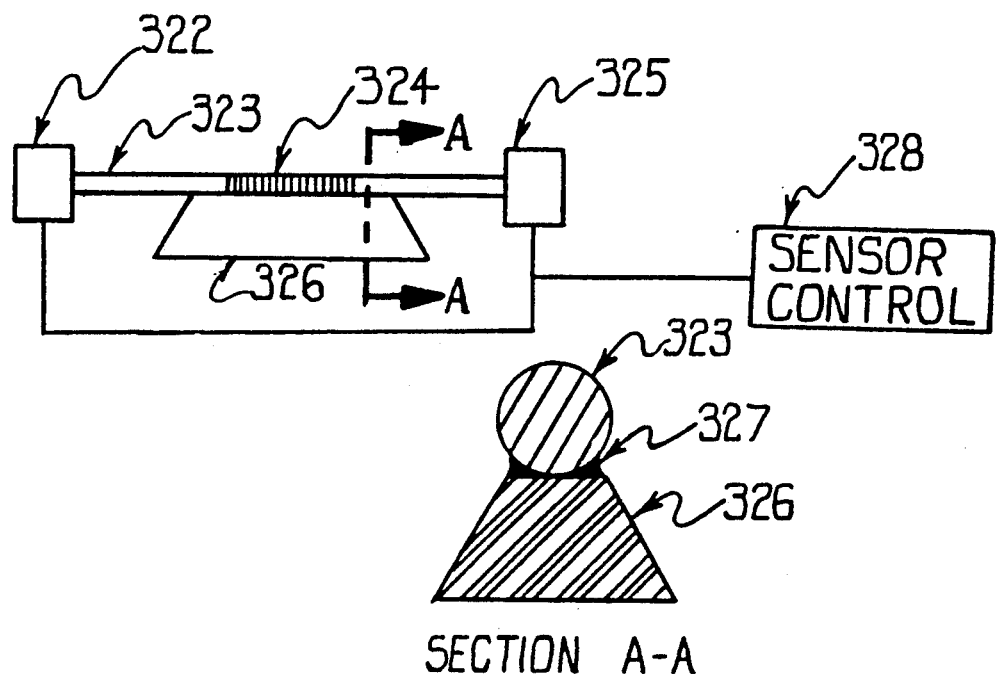
FIG. 18 is a representation of an alternate configuration of the optical path sensor apparatus where the optical path material is supported by a structural pedestal.

FIG. 18 shows sensor apparatus comprising a light source means 322, such as a conventional infrared light emitting diode (LED) for generating light when connected to a power supply. An optical path such as a fiber optic cable means 323 is connected at one end to the light source means 322 for transmitting light beams along the fiber optic cable means 323 to the other end of the fiber optic cable means which is connected to conventional light receiving and signal generating detector means 318, such as conventional light receiving device (LRD), for generating variable output signals which vary in accordance with the amount of light transmitted thereto. The sensor apparatus is electrically connected to the sensor control 328. Power required by the light source means 322 and light detector means 325 is provided by the sensor control 328; and the light detector signal output is processed by the sensor control 328 and result is interfaced to conventional alarm systems, power shut-offs, machine controllers and the like. The fiber optic cable means 323 is of conventional design, except as modified as herein described, and comprises one or more core fibers having a generally cylindrical outer peripheral surface configuration. The entire outer surface of the optical fiber or fibers is conventionally covered by an optical coating or cladding material which prevents lateral transmission of light while enabling only longitudinal transmission of light. An optical path sensor portion 324 is operably associated with the optical path means 323 to provide a section in the light transmission path wherein the amount of light traveling through the optical light path means is varied in accordance with the detection of the sensed medium in an environment circumjacent to the sensor portion 324 whereby an output signal from detector means 325 is varied in accordance with the adsorption and absorption by the sensor portion 324 of the sensed medium. The sensor portion 324 is a section of the optical path means where the coating or cladding has been removed to provide an exposed peripheral area to be in contact with the sense medium. Alternatively, the optical path 323 could be provided by molding the transparent material in an elongated shape bridging the light source means 322 and light detector means 325 at each end of the molding. The peripheral surface area of the sensor portion 324 may be increased by transverse striations which may be formed by sanding the peripheral surface of the core fiber or fibers, in a transverse direction, with abrading material such as sandpaper and the like. Such transverse striations may also be obtained by rotating a pointed cutting tool around the outermost surface of the optical fiber means. For example, such striations may be cut at 0.2 mm apart with a 60 degree cutter to a depth of 0.2 mm. It is experimentally demonstrated that small amount of bending of the sensor portion 324 causes a large attenuation of the light transmitted along the optical path. Such attenuation due to bending impairs the sensitivity of the sensor apparatus. To minimize attenuation due to bending of the sensor portion 324, a support means 326 is attached to the sensor portion 324 with adhesives and the like to provide structural rigidity to the sensor portion 324.

Figure 16:
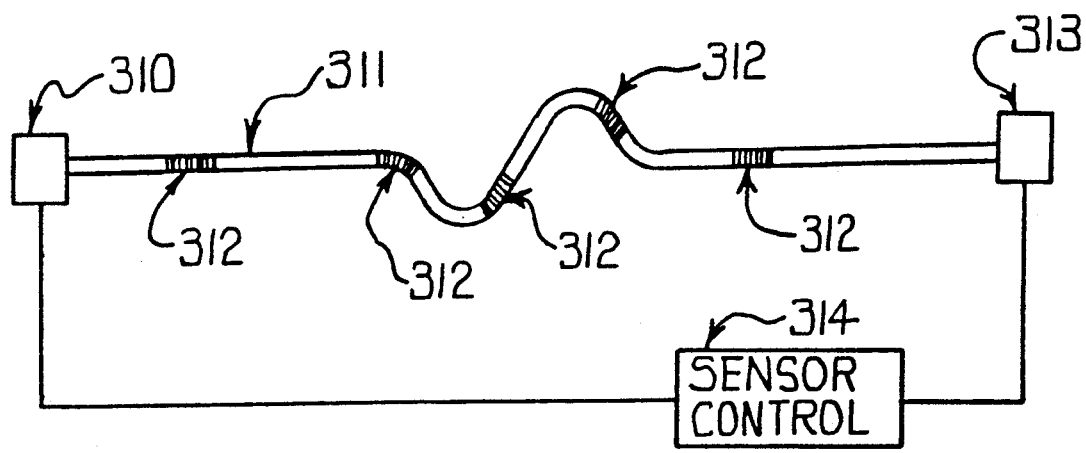
FIG. 16 is a representation of an alternate configuration of the optical path sensor apparatus where the optical fiber is processed such that there are more than one sensor portions along the length of the optic path means.

FIG. 16 shows a sensor apparatus comprising a light source means 310, such as a conventional infrared light emitting diode (LED) for generating light when connected to a power supply. An optical path such as a fiber optic cable means 311 is connected at one end to the light source means 310 for transmitting light beams along the fiber optic cable means 311 to the other end of the fiber optic cable means which is connected to conventional light receiving and signal generating detector means 313, such as conventional light receiving device (LRD), for generating variable output signals which vary in accordance with the amount of light transmitted thereto. The sensor apparatus is electrically connected to the sensor control 314. Power required by the light source means 310 and light detector means 313 is provided by the sensor control 314; and the light detector signal output is processed by the sensor control 314 and the result is interfaced to conventional alarm systems, power shut-offs, machine controllers and the like. Optical path sensor portions 312 is operably associated with the optical path means 311 to provide sections in the light transmission path wherein the amount of light traveling through the optical light path means is varied in accordance with the detection of the sensed medium in an environment circumjacent to the sensor portions 312 whereby an output signal from detector means 313 is varied in accordance with the adsorption and absorption by the sensor portions 312 of the sensed medium. The sensor portions 312 is a section of the optical path means where the coating or cladding has been removed to provide an exposed peripheral area to be in contact with the sensed medium. Alternatively, the optical path 311 could be provided by molding the transparent material in an elongated shape bridging the light source means 310 and light detector means 313 at each end of the molding. The peripheral surface area of the sensor portions 312 may be increased by transverse striations which may be formed by sanding the peripheral surface of the core fiber or fibers, in a transverse direction, with abrading material such as sandpaper and the like. Such transverse striations may also be obtained by rotating a pointed cutting tool around the outermost surface of the optical fiber means. For example, such striations may be cut at 0.2 mm apart with a 60 degree cutter to a depth of 0.2 mm.

The herein described sensor apparatus of FIGS. 14, 16, 19, 21, etc. is suitable for fluid detection in long and irregular shaped cavities where the optical path could be laid to conform to the cavity contour. For example, such sensor apparatus may be employed in the wing cavities of an aircraft for fuel leak detection.

Figure 20:
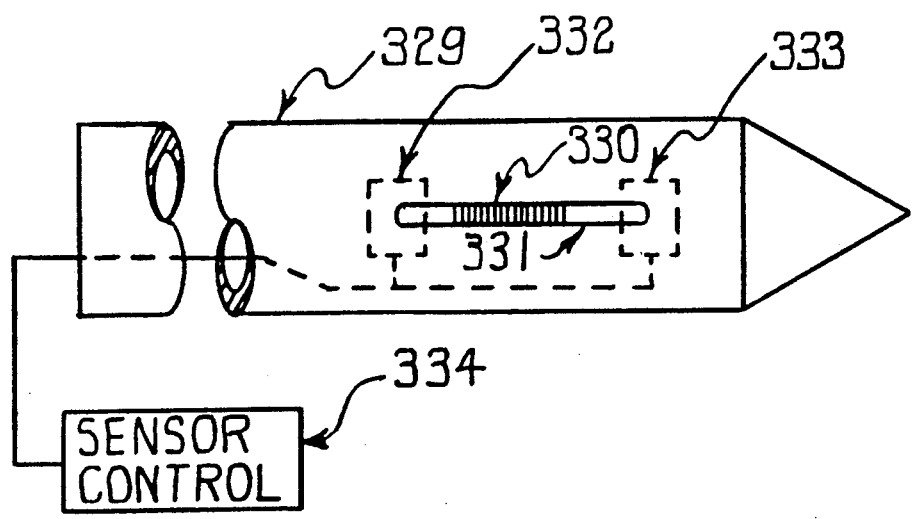
FIG. 20 is a representation of an alternate configuration of the optical path sensor apparatus where the sensor portion is located on the surface of a pointed stake.

FIG. 20 shows sensor apparatus comprising a light source means 333, such as a conventional infrared light emitting diode (LED) for generating light when connected to a power supply. An optical path such as a fiber optic cable means 331 is connected at one end to the light source means 333 for transmitting light beams along the fiber optic cable means 331 to the other end of the fiber optic cable means which is connected to conventional light receiving and signal generating detector means 332, such as conventional light receiving device (LRD), for generating variable output signals which vary in accordance with the amount of light transmitted thereto. The sensor apparatus is electrically connected to the sensor control 334. Power required by the light source means 333 and light detector means 332 is provided by the sensor control 334; and the light detector signal output is processed by the sensor control 334 and the result is interfaced to conventional alarm systems, power shut-offs, machine controllers and the like. An optical path sensor portion 330 is operably associated with the optical path means 331 to provide a section in the light transmission path wherein the amount of light traveling through the optical light path means is varied in accordance with the detection of the sensed medium in an environment circumjacent to the sensor portion 330 whereby an output signal from detector means 332 is varied in accordance with the adsorption and absorption by the sensor portion 330 of the sensed medium. The sensor portion 330 is a section of the optical path means where the coating or cladding has been removed to provide an exposed peripheral area to be in contact with the sensed medium. Alternatively, the optical path 331 could be provided by molding transparent material in an elongated shape bridging the light source means 333 and light detector means 332 at each end of the molding. The peripheral surface area of the sensor portion 330 may be increased by transverse striations which may be formed by sanding the peripheral surface of the core fiber or fibers, in a transverse direction, with abrading material such as sandpaper and the like. Such transverse striations may also be obtained by rotating a pointed cutting tool around the outermost surface of the optical fiber means. For example, such striations may be cut at 0.2 mm apart with a 60 degree cutter to a depth of 0.2 mm. The sensor apparatus is mounted on a pointed stake 329 such that the optical path sensor portion 330 of the sensor apparatus are located on the outer surface of the stake while the remainder of the apparatus is located in the inside of the stake. The electrical wiring connecting the sensor apparatus and the sensor control 334 is routed inside of the stake and out the blunt end. The sensor apparatus thus mounted on the stake can be used to sense the interior of a relatively soft bulk substance such as moist soil, stored grain, etc. by inserting the stake into the bulk substance.

FLUID LEVEL SENSOR

Figure 21:
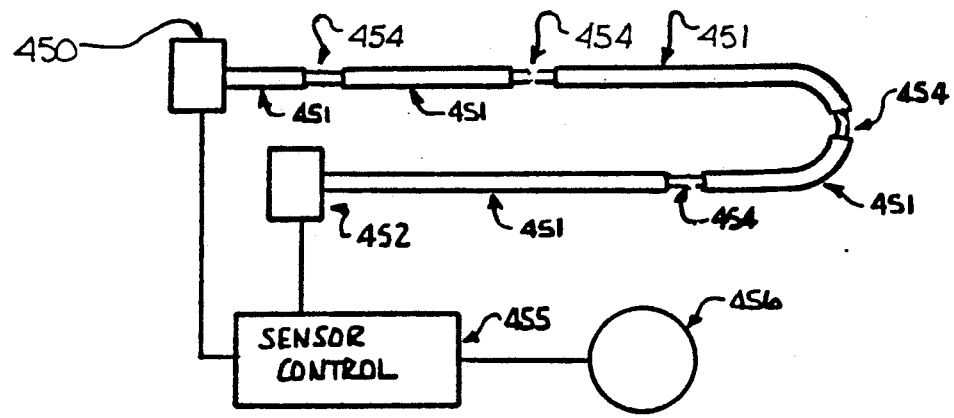
FIG. 21 is a pictorial representation of a containment vessel level sensor utilizing a medium sensor constructed in accordance with the teachings of the present invention.

In general, as shown in FIG. 21, the present preferred embodiment employs a light source means 450, such as a conventional infrared light emitting diode (LED) for generating light when connected to a power supply within the sensor control means 455. A fiber optic cable means 451 is connected at one end to the light source means 450 for continuously transmitting light beams along the fiber optic cable means which is connected to conventional light receiving and signal generating detector means 452, such as conventional light receiving device (LRD), for generating variable output signals which vary in accordance with the amount of light transmitted thereto. The light source means 450 and light receiving and signal generating means 452 which is arranged to provide an output in conventional manner usable for the control of process variables 456. The fiber optic cable means 451 is of conventional design except as modified as herein described, and comprises one or more core fibers 453 having a generally cylindrical outer peripheral surface configuration. The entire outer surface of the optical fiber or fibers is conventionally covered by an optical coating or cladding material which prevents lateral transmission of light while enabling only longitudinal transmission of light. A condition sensing sensor portion or portions means 454 is operably associated with the fiber optic cable means to provide a section in the light transmission path wherein the amount of light traveling through the fiber optic cable means is varied in accordance with a change in the condition of the sensed medium in an environment associated with the sensing portion or portions means 454 whereby an output signal from the detector means 452 is varied in accordance with the presence and change of condition of the sensed medium. The sensing portion or portions means 454 is a section or sections of the fiber optic means where the coating or cladding has been removed to provide an exposed sensed medium area or areas in which the core fiber or fibers have no cladding precluding transfer of a portion of the light therethrough. The outermost surface portion of the sensing portion or portions 454 is provided with transverse striations thereacross which may be formed during the removal of the coating material by sanding the peripheral surface of the core fiber or fibers in one or more areas with abrading material such as a piece of sandpaper or the like. Alternatively, transverse striations may be obtained by the action of a pointed cutting tool rotated around the outermost surface of the optical fiber means.

The aforementioned apparatus and method for detecting the presence and changes in the condition of a sensed medium are based upon the use of the differences of refractive indices, absorbance and reflectance of the different sensed mediums.

The fiber optic portion having a striated or abraded peripheral surface for providing a sensor portion or portions means, may be striated or abraded in a manner that light losses from the sensor portion or portions of the fiber optic provide a direct proportionality between the surface area of the sensor portion or portions in contact with the sensed medium and the generated output signals of the light receiving device. Likewise, the fiber optic portion having a striated or abraded peripheral surface for providing a sensor portion or portions means, may be striated or abraded in a manner that light losses from the sensor portion or portions of the fiber optic provide an mathematically definable indirect proportionality between the surface area in contact with the sensed medium and the generated output signals of the light receiving device.

The amount of light losses in the sensor portion or portions of the fiber optic means is proportional to the number of striations or abrasion scratches thereon and the length or size of the sensor portion. By placing more striations or scratches in a certain selected sensor portion or portions or regions or portions thereof, light losses in those certain areas are caused to be greater than in otherwise equivalent sensor portion or portions or regions or portions thereof having fewer striations or abrasion scratches. The magnitude of light losses from the areas having more surface striations or abrasion scratches will be changed more in absolute amount by contact with the sensed medium than will the light losses in sensor portions having less light losses. The amount of light received by the light receiving device and the signal produced thereby will be in proportion to the total light transmitted less the losses occurring at the sensor portion or portions. By placing more striations or abrasion scratches in a sensor portion or portions, a sensor portion or portions of greater sensitivity than other sensor portions or regions thereof on the optical fiber means is created where the term sensitivity is defined as absolute change in light losses per unit of sensor portion surface area in contact with the sensed medium.

The following describes preferred method for fabrication of a sensor portion by sanding the outer surface of a one millimeter diameter clad acrylic multi-mode optical fiber of conventional design so as to create at least two sensing areas having sensitivity to a sensed medium different from each other in absolute terms as defined previously. To create striations perpendicular to the longitudinal axis of the optical fiber sensor portion or portions by sanding its outer surface, the portion of the optical fiber to be striated is held against the optical fiber with an approximate normal force between the optical fiber and the sand paper of one ounce per linear inch of optical fiber to be striated. While under the aforestated normal force condition, the fiber is rotated against the surface of the sandpaper. During rotation, the fiber is not permitted to translate in the fiber longitudinal direction relative to the surface of the sandpaper thereby avoiding the creation of striations parallel to the longitudinal axis of the fiber sensor portion. To control the amount of surface abrasion or striations produced by this process, the number of revolutions made by the optical fiber while the sensor portion is in contact with the sanding surface is varied to suit the application. If, for example, a sensor is desired having two sensor portions of differing absolute sensitivity, a first portion having low absolute sensitivity relative to the second and the second having high absolute sensitivity relative to the first sensor portion where sensitivity is as previously defined, each portion having a length of one inch and the sensor portions located adjacent to each other on the same fiber optic means, the following describes a preferred method of fabrication by sanding. The first low sensitivity sensor portion is striated by rotation of its outer surface against the surface of sandpaper as described above for one-half to three-fourths of one revolution of the fiber. The second high absolute sensitivity sensor portion is striated by rotation of its outer surface as described above for five complete revolutions of the fiber. High and low absolute sensitivity fiber sensor portions fabricated as described herein were determined to have differing sensitivity to the absence or presence of liquid water. The difference in the attenuation of light passing through the sensor portion when the sensor portion is dry compared to when the sensor portion is wet with liquid water was found to be four times greater for the high sensitivity more highly striated fiber than for the low sensitivity less striated fiber.

Figure 22:
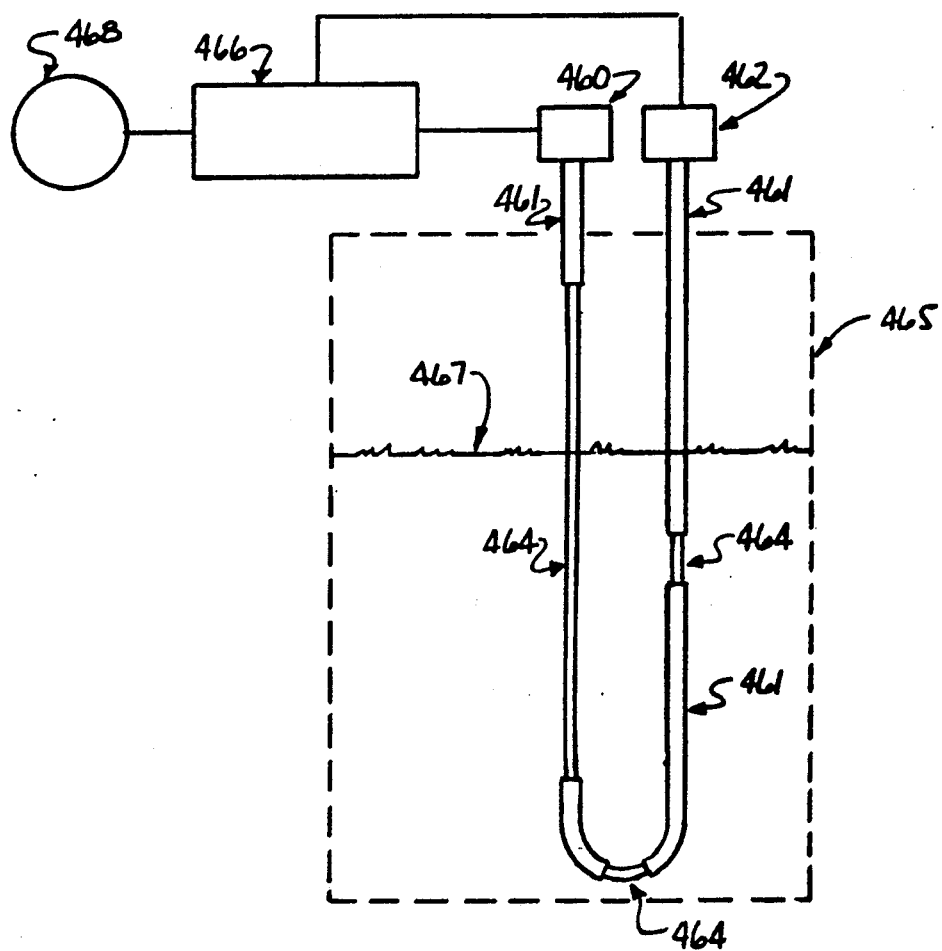
FIG. 22 is a representation of a containment vessel level sensor utilizing a plurality of sensor portions arranged along a generally vertical fiber optic cable means.

In one embodiment, as shown in FIG. 22, the aforedescribed sensor is used as a containment vessel level sensor. The sensed medium may be petroleum distillates such as gasoline. Referring to FIG. 22, the sensor apparatus as aforedescribed comprising light source means 460, fiber optic means 461 and light detection and signal generating means 462 is arranged vertically in a containment vessel 465 with sensor portion or portions 464 located at a position or positions of interest for the purpose of sensing the level of medium 467 in the containment vessel 465 in order to control a process or processes 468 related thereto. The sensor apparatus is operably connected to the sensor control means 466. Power required by the light source means 460 and light detector means 462 is provided by the sensor control means 466; and the light detector means 462 signal output is processed by the sensor control means 466. Varying the amount of petroleum distillate in the containment vessel causes variation in the surface area of the sensor portion or portions that are wetted, in contact, or covered by the sensed medium. This causes the light transmitted through the fiber optic cable 461 to vary which variation is detected by the light detection means 462 causing a corresponding signal to be produced thereby which varies in a predictable manner with the level of liquid in the containment vessel. Upon a predetermined signal level or levels from the light detector means 462, alarms, pumps, heaters and other process devices may be activated or deactivated by the sensor control means 466 depending upon the specific application wherein the sensor is employed. Alternatively, the sensor control means may contain a timing device of conventional design by which means the rate of change of medium level 467 within a containment vessel 465 level may be determined by the control means 466 using conventional algorithms developed by others for this purpose. For example, using the cross sectional area dimension of the containment vessel and the rate of change of the height of the medium 467 in the vessel 465 will allow calculation of the rate of medium transfer into or out of the containment vessel 465 to be calculated by the sensor control means 466 using conventional arithmetic. A special situation where this is applicable is the determination of whether medium is leaking out of the containment vessel 465 which will be evident by falling medium level 467 in the containment vessel absent any other deliberate control or pumping activity. Likewise, a second medium leaking into the containment vessel 465 may be sensed by rising medium level in the containment vessel 467 absent any other deliberate control or pumping activity. In the aforedescribed preferred embodiment, the number of striations or scratches on the surface of the fiber 461 at sensing portion or portions means 461 of FIG. 21 are uniformly placed on the sensing portion or portions.

Figure 23:
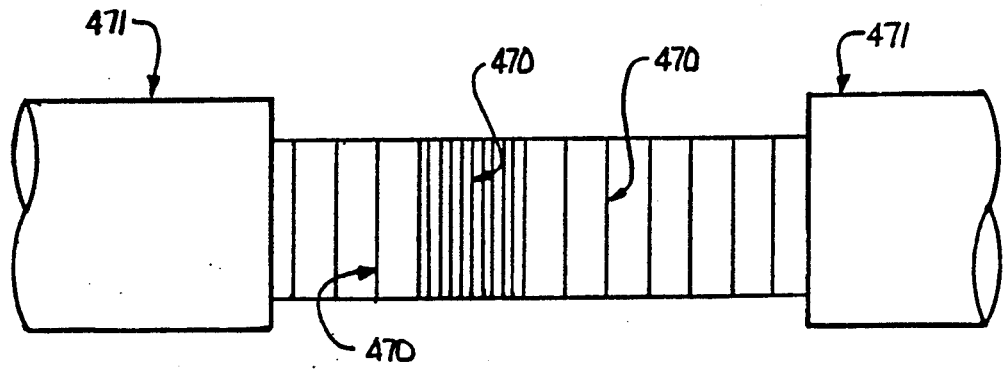
FIG. 23 is a representation of an alternate configuration of a fiber optic sensor portion wherein the number of striations per unit of surface area is different in one region of the sensor portion than in other regions of the sensor portion.

In another presently preferred embodiment illustrated by FIGS. 23 and 25, the number of aforedescribed striations or scratches 470 on the surface of the aforedescribed fiber sensing means 471 is not uniform; there being more striations or scratches 470 made on the surface of the fiber sensing means 476 in one or more aforedescribed sensor portions 472 which are to be placed within a containment vessel 473 at aforedescribed locations 474 of special interest where greater medium level 475 measurement resolution or sensitivity is desired.

Figure 24:
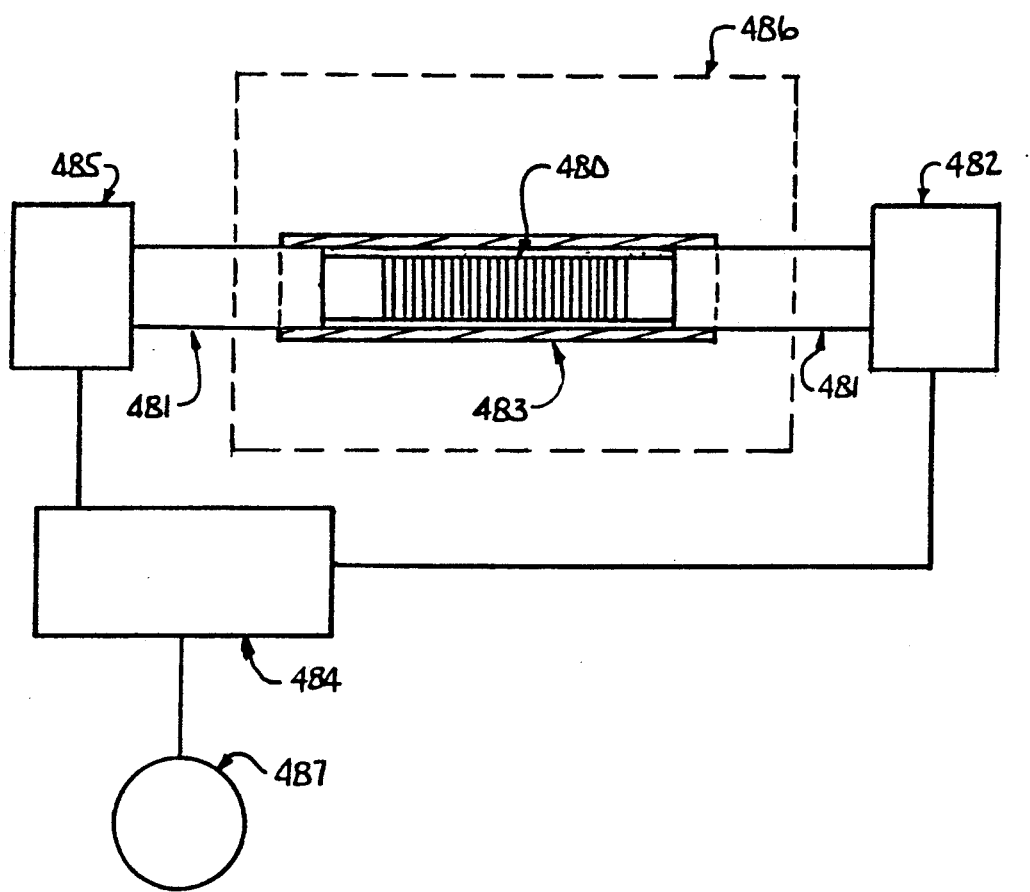
FIG. 24 is a representation of an alternate configuration of a fiber optic sensor portion wherein the sensor portion is coated or covered by a selectively permeable coating or membrane.

In the embodiment illustrated in FIG. 24, the aforedescribed fiber sensing portion or portions means 480 is operably associated with the aforedescribed fiber optic cable means 481 to provide a section in the light transmission path wherein the amount of light from the aforedescribed light source means 485 travels through the fiber optic cable means 481 and is varied in accordance with the presence of a sensed medium in an environment 486 such as a containment vessel associated with the sensing portion or portions means 480 whereby an output signal from detector means 482 is varied in accordance with the detection of the sensed medium. The sensing portion means 480 is a section of the fiber optic material where the coating or cladding has been removed to provide an exposed sensed medium portion in which the core fiber or fibers have no outer peripheral cladding precluding transfer of a portion of the light therethrough. The outer peripheral surface of the sensing portion or portions means 480 is provided with transverse striations thereacross which may be formed during removal of the coating material by sanding the peripheral surface of the core fiber or fibers with abrading material such as a piece of sandpaper and the like. Alternatively, such transverse striations may be obtained by rotary cutting with a pointed cutting tool around the outermost surface of the optical fiber means. A covering means 483 is applied over the sensing portion or portions means 480, and is of a substance that is selectively permeable to the sensed medium. The covering means is preferably constructed such that a small crack or annular coaxial open space 488 is created between the inner surface of the covering means 489 and the outer surface 490 of the optical fiber sensor portion 480 into which the sensed medium may permeate from the environment 486 through the covering 483 to contact the surface 490 of the sensing portion 480 of the optical fiber means 481. For example, the covering means 483 may be of a semi-permeable substance that may be permeated by substances of less than 1000 molecular weight but retain or block from permeation substances of higher molecular weight. Abcor ultra filtration membrane model number MSD-238 is an example of such a material. Reverse osmosis membranes may also be used as a covering means 483 for the purpose of selective permeation of substances from the environment 487. Therefore the herein described sensor apparatus may be immersed in media other than water without causing the sensor portion means 480 to be in contact with the media; however, if water is introduced into the environment 486, the permeable coating means 483 allows water present in the environment to penetrate the coating means 483 and contact the sensor portion means 480 causing a signal level change to be output to the sensor control means 484 where the signal is processed to interface with conventional alarm systems, power shut-offs, machine controllers and the like 487.

The invention has been described by reference to various illustrative embodiments including various forms of apparatus with particular embodiments which may be employed with other embodiments. It is intended that the appended claims be construed to cover various alternative embodiments and modifications except insofar as limited by the prior art.

What is claimed is:

1. A system for detection of a selected medium in an environment comprising:
   a light source means for generating a beam of light;
   a light receiving and signal generating means for receiving light from said light source and for generating variable signals dependent upon the amount of light received;
   optical path means made of a continuous uninterrupted length of transparent material for connecting said light source means to said light receiving and signal generating means and for providing a continuous light path therebetween for transmitting said beam of light from said light source means to said light receiving means along the optical path;
   at least one sensor portion located on a peripheral outer surface of said optical path means and in contact with the environment and being constructed and arranged to cause change in intensity of light transmitted through said sensor portion dependent on the amount of selected medium in the environment adsorbed and absorbed by the sensor portion, whereby variable output signals generated by said light receiving and signal generating means vary in accordance with the amount of selected medium in the environment adsorbed and absorbed by the sensor portion; and
   signal processing and indicating means connected to said light receiving and signal generating means for output signaling and for indicating the detection of the selected medium in the environment.

2. The invention as defined in claim 1 and wherein: said sensor portion of said optical path means has an outer surface with striation grooves extending generally laterally relative to the central axis of said optical path means.

3. The invention as defined in claims 1 or 2 wherein: the sensor portion is covered with a dissolvable substance that is selectively dissolvable to a selected sensed medium.

4. The invention as defined in claims 1 or 2 wherein: the sensor portion is covered with a permeable substance that is selectively permeable to a selected sensed medium.

5. The invention as defined in claims 1 or 2 wherein: the sensor portion is attached to a structural support with adhesive-like material to provide rigidity to the sensor portion.

6. The invention as defined in claims 1 or 2 wherein: the sensor portion of the optical path means is of a chemically reactive material that chemically reacts to the selected sensed medium such that the optical property and physical property of the optical path means changes.

7. The invention as defined in claims 1 or 2 wherein: optical path means containing the sensor portion is subjected to tension by a spring means; and the material of the optical path means is such that it weakens when in contact with the selected sensed medium whereby the spring means breaks the optical path means.

8. The invention as defined in claims 1 or 2 wherein: the optical path means containing the sensor portion is mounted on the outer surface of a pointed stake; the remainder of the apparatus is located inside the stake and the signal wiring is routed through the blunt end of the stake.

9. The invention as defined in claim 1 wherein the optical path means comprises:
   a "Y" shape assembly having three lengths of transparent material.

10. The invention as defined in claim 9 and wherein:
    two of the lengths of the optical path means subtend an angle less than 90 degrees; these two legs are connected to the light source means and the light detector and signal generating means; and
    the third length of the optical path means contains the sensor portion and the end of which is polished and coated with a reflective coating whereby the light beam from the light source means is reflected back and a portion of this reflected light is transmitted to the light receiving and signal generating means.

11. The invention as defined in claim 1 wherein:
    there are more than one sensor portion located in spaced relationship along the length of the optical path means.

12. A system for detection of a change of condition in an environment comprising:
    fiber optical tube means having an elongated passage therein with a light inlet portion for receiving a beam of light and a light outlet portion for discharging the beam of light;
    an intermediate portion of said fiber optical tube means having an exterior surface providing a light transmission opening means for enabling passage of a portion of the light beam therethrough;
    light measuring means associated with said outlet portion of said fiber optical tube means for measuring the amount of light transmitted thereto and for generating signals indicative of the amount of light received thereby;
    said exterior surface of light transmission opening means being located in the environment and being subject to changes in environmental conditions adjacent thereto for changing the amount of light transmitted through said light transmission opening means and the amount of light transmitted to said light measuring means; and
    condition indicating means connected to said light measuring means for indicating the presence of a selected substance adjacent said exterior surface of said light transmission opening means.

13. The invention as defined in claim 12 and wherein:
    said exterior surface of said intermediate portion of said fiber optical tube means having a non-smooth roughened exterior surface with striations extending transversely to the axis of the light beam.

14. The invention as defined in claim 13 and wherein said intermediate portion of said light transmission means comprises:
    an U-shape loop section having a curved portion connecting a pair of straight elongated sections whereby the light beam path changes direction while passing through the U-shape loop portion.

15. The invention as defined in claims 1 or 13 and being employed as an optical soil moisture detection an irrigation control apparatus, wherein:
    the sensor portion of the apparatus is buried in the soil under agricultural crops; and
    the sensor control of the apparatus is interfaced to a conventional sprinkler or irrigation control system.

16. The invention as defined in claims 1 or 13 and being employed as an optical soil contamination detection apparatus wherein:

the sensor portion of the apparatus is installed in the filler material near an underground storage tank; and the sensor control of the apparatus is interfaced to a conventional alarm system and or other electrical controllers.

17. The invention as defined in claims 1 or 13 and being employed as an optical leak detection apparatus wherein:

the sensor portion of the apparatus is installed in the annular space between the outer and inner walls of a double walled storage tank; and sensor control of the apparatus is interfaced to a conventional alarm system and or other electrical controllers.

18. The invention as defined in claim 12 and wherein:

said exterior surface of said intermediate portion having striation grooves extending generally laterally relative to the central axis of said light transmission means.

* * * * *